US010265439B2

(12) United States Patent
Nikkhah et al.

(10) Patent No.: US 10,265,439 B2
(45) Date of Patent: Apr. 23, 2019

(54) INJECTABLE CELL-LADEN BIOHYBRID HYDROGELS FOR CARDIAC REGENERATION AND RELATED APPLICATIONS

(71) Applicant: ARIZONA BOARD OF REGENTS ON BEHALF OF ARIZONA STATE UNIVERSITY, Scottsdale, AZ (US)

(72) Inventors: Mehdi Nikkhah, Scottsdale, AZ (US); Brent Vernon, San Tan Valley, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 54 days.

(21) Appl. No.: 15/242,039

(22) Filed: Aug. 19, 2016

(65) Prior Publication Data
US 2017/0065746 A1    Mar. 9, 2017

Related U.S. Application Data

(60) Provisional application No. 62/214,054, filed on Sep. 3, 2015.

(51) Int. Cl.
| | |
|---|---|
| A61L 27/52 | (2006.01) |
| A61K 38/18 | (2006.01) |
| A61L 27/54 | (2006.01) |
| A61L 27/38 | (2006.01) |
| A61L 27/26 | (2006.01) |
| A61K 9/00  | (2006.01) |
| C12N 5/077 | (2010.01) |
| C12N 5/00  | (2006.01) |

(52) U.S. Cl.
CPC ............ *A61L 27/52* (2013.01); *A61K 9/0024* (2013.01); *A61K 38/1866* (2013.01); *A61L 27/26* (2013.01); *A61L 27/3808* (2013.01); *A61L 27/3826* (2013.01); *A61L 27/54* (2013.01); *C12N 5/0068* (2013.01); *C12N 5/0657* (2013.01); *A61L 2300/252* (2013.01); *A61L 2300/414* (2013.01); *A61L 2400/06* (2013.01); *A61L 2430/20* (2013.01); *C12N 2513/00* (2013.01); *C12N 2533/30* (2013.01); *C12N 2533/54* (2013.01); *C12N 2539/00* (2013.01)

(58) Field of Classification Search
CPC .... A61L 2300/252; A61L 27/26; A61L 27/52; C12N 2533/30; C12N 5/0657
See application file for complete search history.

(56) References Cited

U.S. PATENT DOCUMENTS

| | | | |
|---|---|---|---|
| 7,396,537 B1 | 7/2008 | Krupnick et al. | |
| 2005/0037082 A1 | 2/2005 | Wan et al. | |
| 2008/0050435 A1 | 2/2008 | Hennink et al. | |
| 2008/0069801 A1 | 3/2008 | Lee et al. | |
| 2008/0082163 A1 | 4/2008 | Woo et al. | |
| 2008/0096975 A1 | 4/2008 | Guan et al. | |
| 2009/0053276 A1 | 2/2009 | Richard | |
| 2010/0215749 A1 | 8/2010 | Stayton et al. | |
| 2011/0097406 A1 | 4/2011 | Bryant et al. | |
| 2012/0034271 A1* | 2/2012 | Shu ..................... | A61K 9/0019 424/400 |
| 2014/0256617 A1 | 9/2014 | Overstreet et al. | |
| 2014/0288189 A1 | 9/2014 | Overstreet et al. | |
| 2017/0143871 A1 | 5/2017 | Nikkhah et al. | |

FOREIGN PATENT DOCUMENTS

| | | |
|---|---|---|
| WO | 2013056167 A1 | 4/2013 |
| WO | 2013056170 A1 | 4/2013 |

OTHER PUBLICATIONS

Li et al. Hydrogels for cardiac tissue engineering. Polymers. 2011;3:740-761.*
Kang, et al., "PDGF-A as an epicardial mitogen during heart development", Dev Dyn 237(3), 692-701 (2008).
Kattman, et al., "Stage-Specific Optimization of Activin/Nodal and BMP Signaling Promotes Cardiac Differentiation of Mouse and Human Pluripotent Stem Cell Lines", Cell Stem Cell 8(2), 228-240 (2011).
Kaully, et al., "Vascularization—The Conduit to Viable Engineered Tissues", Tissue Eng Part B Rev 15(2):159-169 (2009).
Khademhosseini, et al., "Microscale technologies for tissue engineering and biology", Proc Natl Acad Sci U S A 103(8), 2480-2487 (2006).
Kharaziha, et al., "PGS: Gelatin nanofibrous scaffolds with tunable mechanical and structural properties for engineering cardiac tissues", Biomaterials 34(27), 6355-6366 (2013).
Kharaziha, et al., "Tough and flexible CNT-polymeric hybrid scaffolds for engineering cardiac constructs", Biomaterials 35(26), 7346-7354 (2014).
Kofidis, et al., "Injectable bioartificial myocardial tissue for large-scale intramural cell transfer and functional recovery of injured heart muscle", J Thoracic Cardiovasc Surg 128(4), 571-578 (2004).
Kohl, "Heterogeneous cell coupling in the heart—an electrophysiological role for fibroblasts", Circ Res 93(5), 381-383 (2003).
Kutschka, et al., "Collagen matrices enhance survival of transplanted cardiomyoblasts and contribute to functional improvement of ischemic rat hearts", Circulation 114(1 Suppl), I167-I173 (2006).
LaFlamme, et al., "Heart regeneration", Nature 473(7347), 326-335 (2011).
Lavine, et al., "Endocardial and epicardial derived FGF signals regulate myocardial proliferation and differentiation in vivo", Dev Cell 8(1), 85-95 (2005).

(Continued)

*Primary Examiner* — Lynn Y Fan
(74) *Attorney, Agent, or Firm* — Viksnins Harris Padys Malen LLP

(57) ABSTRACT

The present invention provides a temperature-responsive dual-gelling hydrogel comprising a plurality of hydrogel polymers and a polymer cross-linking moiety, wherein the LCST of the hydrogel polymers is less than 37° C., and the polymer cross-linking moiety is capable of chemically cross linking to the hydrogel polymers to form a polymer matrix.

20 Claims, 12 Drawing Sheets

Specification includes a Sequence Listing.

(56) References Cited

OTHER PUBLICATIONS

Lee, et al., "An in situ Injectable Physically and Chemically Gelling NIPAAm-based Copolymer System for Embolization", Biomacromolecules 7(6), 2059-2064 (2006).
Lee, et al., "Copolymers of N-isopropylacrylamide, HEMA-lactate and acrylic acid with time-dependent lower critical solution temperature as a bioresorbable carrier", Polym Int 54(2), 418-422 (2005).
Lee, et al., "In Situ-Gelling, Erodible N-isopropylacrylamide Copolymers", Macromol Biosci 5(7), 629-635 (2005).
Leor, et al., "Bioengineered cardiac grafts: a new approach to repair the infarcted myocardium?", Circulation 102(19 Suppl 3): III56-III61 (2000).
Leri, et al., "Myocardial regeneration and stem cell repair", Curr Probl Cardiol 33(3), 91-153 (2008).
Li, et al., "A PNIPAAm-based thermosensitive hydrogel containing SWCNTs for stem cell transplantation in myocardial repair", Biomaterials 35(22), 5679-5688 (2014).
Little, et al., "Engineering biomaterials for synthetic neural stem cell microenvironments", Chem Rev 108(5), 1787-1796 (2008).
Lovett, et al., "Vascularization Strategies for Tissue Engineering", Tissue Eng Part B Rev 15(3), 353-370 (2009).
Lu, et al., "Both the transplantation of somatic cell nuclear transfer- and fertilization-derived mouse embryonic stem cells with temperature-responsive chitosan hydrogel improve myocardial performance in infarcted rat hearts", Tissue Eng Part A 16(4), 1303-1315 (2010).
Lu, et al., "Functional improvement of infarcted heart by co-injection of embryonic stem cells with temperature-responsive chitosan hydrogel", Tissue Eng Part A 15(6), 1437-1447 (2009).
Matsubayashi, et al., "Improved left ventricular aneurysm repair with bioengineered vascular smooth muscle grafts", Circulation 108(10), II219-II225 (2003).
Moon, et al., "Micropatterning of Poly(Ethylene Glycol) Diacrylate Hydrogels with Biomolecules to Regulate and Guide Endothelial Morphogenesis", Tissue Eng Part A 15(3), 579-585 (2009).
Moon, et al., "Vascularization of engineered tissues: Approaches to promote angiogenesis in biomaterials", Curr Top Med Chem 8(4), 300-310 (2008).
Mouquet, et al., "Restoration of cardiac progenitor cells after myocardial infarction by self-proliferation and selective homing of bone marrow-derived stem cells", Circ Res 97(11), 1090-1092 (2005).
Muller-Ehmsen, et al., "Survival and development of neonatal rat cardiomyocytes transplanted into adult myocardium", J Mol Cell Cardiol 34(2), 107-116 (2002).
Nakajima, et al., "Gelatin hydrogel enhances the engraftment of transplanted cardiomyocytes and angiogenesis to ameliorate cardiac function after myocardial infarction", PLoS One 10(7), e0133308, 11 pages (2015).
Nelson, et al., "Intramyocardial injection of a synthetic hydrogel with delivery of bFGF and IGF1 in a rat model of ischemic cardiomyopathy", Biomacromolecules 15(1), 1-11 (2014).
Nelson, et al., "Repair of Acute Myocardial Infarction by Human Stemness Factors Induced Pluripotent Stem Cells", Circulation 120(5), 408-416 (2009).
Nicodemus, et al., "Cell encapsulation in biodegradable hydrogels for tissue engineering applications", Tissue Eng Part B Rev 14(2), 149-165 (2008).
Nikkhah, et al., "Directed endothelial cell morphogenesis in micropatterned gelatin methacrylate hydrogels", Biomaterials 33, 9009-9018 (2012).
Nikkhah, et al., "Isotropically Etched Silicon Microarrays for Rapid Breast Cancer Cell Capture", IEEE Sensors Journal 13(3), 1125-1132 (2013).
Nugent, et al., "Tissue engineering therapy for cardiovascular disease", Circ Res 92(10), 1068-1078 (2003).
Oh, et al., "Cardiac progenitor cells from adult myocardium: Homing, differentiation, and fusion after infarction", Proc Natl Acad Sci U S A 100(21), 12313-12318 (2003).
Orlic, et al., "Bone marrow cells regenerate infarcted myocardium", Nature 410(6829), 701-705 (2001).
Orlic, et al., "Mobilized bone marrow cells repair the infarcted heart, improving function and survival", Proc Natl Acad Sci U S A 98(18), 10344-10349 (2001).
Overstreet, et al., "In situ forming, resorbable graft copolymer hydrogels providing controlled drug release", J Biomed Mater Res Part A 101(5), 1437-1446 (2012).
Overstreet, et al., "Temperature-responsive graft copolymer hydrogels for controlled swelling and drug delivery", Soft Materials 11(3), 294-304 (2013).
Oyama, et al., "Cardiac side population cells have a potential to migrate and differentiate into cardiomyocytes in vitro and in vivo", J Cell Biol 176(3), 329-341 (2007).
Patent Cooperation Treaty, , International Searching Authority, International Preliminary Report on Patentability and Written Opinion for PCT/US2012/060124, 6 pages, dated Apr. 15, 2014.
Patent Cooperation Treaty, International Searching Authority, International Preliminary Report on Patentability and Written Opinion for PCT/US2012/060121, 5 pages, dated Apr. 15, 2014.
Patent Cooperation Treaty, International Searching Authority, International Search Report for PCT/US/2012/060121, 3 pages, dated Mar. 18, 2013.
Patent Cooperation Treaty, International Searching Authority, International Search Report for PCT/US2012/060124, 5 pages, dated Mar. 15, 2013.
Paul, et al., "Injectable graphene oxide/DNAVEGF based hydrogel for vasculogenesis and cardiac repair", ACS Nano 8(8), 8050-8062 (2014).
Pennisi, et al., "Epicardium is required for the full rate of myocyte proliferation and levels of expression of myocyte mitogenic factors FGF2 and its receptor, FGFR-1, but not for transmural myocardial patterning in the embryonic chick heart", Dev Dyn 228(2), 161-172 (2003).
Qyang, et al., "The renewal and differentiation of IsI1(+) cardiovascular progenitors are controlled by a Wnt/beta-catenin pathway", Cell Stem Cell 1(2), 165-179 (2007).
Radisic, et al., "Biomimetic approach to cardiac tissue engineering", Philos Trans R Soc Lond B Biol Sci 362(1484), 1357-1368 (2007).
Reinecke, et al., "Cardiogenic Differentiation and Transdifferentiation of Progenitor Cells", Circ Res 103(10), 1058-1071 (2008).
Reinecke, et al., "Taking the death toll after cardiomyocyte grafting: a reminder of the importance of quantitative biology", J Mol Cell Cardiol 34(3), 251-253 (2002).
Robb, et al., "Simultaneously physically and chemically gelling polymer system utilizing a poly(NIPAAm-co-cysteamine)-based copolymer", Biomacromolecules 8(7), 2294-2300 (2007).
Romano, et al., "Protein-engineered biomaterials: nanoscale mimics of the extracellular matrix", Biochim Biophys Acta 1810(3), 339-349 (2011).
Ryu, et al. "Implantation of bone marrow mononuclear cells using injectable fibrin matrix enhances neovascularization in infarcted myocardium", Biomaterials 26(3), 319-326 (2005).
Saini, et al., "3D cardiac microtissues encapsulated with the co-culture of cardiomyocytes and cardiac fibroblasts", Adv. Healthc. Mater. 4, 1961-1971 (2015).
Schild, "Poly(N-isopropylacrylamide): experiment, theory and application", Prog Polym Sci 17(2), 163-249 (1992).
Segers, et al., "Biomaterials to Enhance Stem Cell Function in the Heart", Circ Res 109(8), 910-922 (2011).
Segers, et al., "Stem-cell therapy for cardiac disease", Nature 451(7181), 937-942 (2008).
Seif-Naraghi, et al., "Safety and efficacy of an injectable extracellular matrix hydrogel for treating myocardial infarction", Sci Transl Med 5(173), doi:10.1126/scitranslmed.3005503, 20 pages (2013).
Shevach, et al., "Omentum ECM-based hydrogel as a platform for cardiac cell delivery", Biomed Mater 10(3), 034106, 11 pages (2015).
Shin, et al., "Carbon-Nanotube-Embedded Hydrogel Sheets for Engineering Cardiac Constructs and Bioactuators", ACS Nano 7(3), 2369-2380 (2013).

(56) References Cited

OTHER PUBLICATIONS

Shu, et al., "Disulfide-crosslinked hyaluronan-gelatin hydrogel films: a covalent mimic of the extracellular matrix for in vito cell growth", Biomaterials 24(21), 3825-3834 (2003).
Sigel, et al., "Regulation of proliferative response of cardiac fibroblasts by transforming growth factor-beta(1)", J Mol cell Cardiol 28(9), 1921-1929 (1996).
Singelyn, et al., "Modulation of material properties of a decellularized myocardial matrix scaffold", Macromol Biosci 11(6), 731-738 (2011).
Smith, et al., "Regenerative potential of cardiosphere-derived cells expanded from percutaneous endomyocardial biopsy specimens", Circulation 115(7), 896-908 (2007).
Smith, et al., "Signals from both sides: Control of cardiac development by the endocardium and epicardium", Semin cell Dev Biol 18(1), 84-89 (2007).
Soonpaa, et al., "Formation of nascent intercalated disks between grafted fetal cardiomyocytes and host myocardium", Science 264(5155), 98-101 (1994).
Souders, et al., "Cardiac fibroblast the renaissance cell", Circ Res 105(12), 1164-1176 (2009).
Soufan, et al., "Regionalized sequence of myocardial cell growth and proliferation characterizes early chamber formation", Circ Res 99(5), 545-552 (2006).
Stuckmann, et al., "Erythropoietin and retinoic acid, secreted from the epicardium, are required for cardiac myocyte proliferation", Dev Biol 255(2), 334-349 (2003).
Suuronen, et al., "Tissue-engineered injectable collagen-based matrices for improved cell delivery and vascularization of ischemic tissue using CD133+ progenitors expanded from the peripheral blood", Circulation 114(1 Suppl), I138-I144 (2006).
Tan, et al., "Injectable, biodegradable hydrogels for tissue engineering applications", Materials 3(3), 1746-1767 (2010).
Tandon, et al., "Electrical stimulation systems for cardiac tissue engineering", Nat Protoc 4(2), 155-173 (2009).
Tekin, et al., "Controlling Spatial Organization of Multiple Cell Types in Defined 3D Geometries", Adv Mat 24(41), 5543-5547 (2012).
Tekin, et al., "Responsive Microgrooves for the Formation of Harvestable Tissue Constructs", Langmuir 27(9), 5671-5679 (2011).
Tekin, et al., "Responsive Micromolds for Sequential Patterning of Hydrogel Microstructures", J Am Chem Soc 133 (33), 12944-12947 (2011).
Tous, et al., "Injectable Acellular Hydrogels for Cardiac Repair", J Cardiovasc Transl Res 4(5), 528-542 (2011).
Vanguilder, et al., "Twenty-five years of quantitative PCR for gene expression analysis", Biotechniques 44(5), 619-626 (2008).
Vercruysse, et al., "Synthesis and in vitro degradation of new polyvalent hydrazide cross-linked hydrogels of hyaluronic acid", Bioconjugate Chem 8(5), 686-694 (1997).
Vintersten, et al., "Mouse in red: Red fluorescent protein expression in mouse ES cells, embryos, and adult animals", Genesis 40(4), 241-246 (2004).
Vunjak-Novakovic, et al., "Challenges in Cardiac Tissue Engineering", Tissue Eng Part B Rev 16(2), 169-187 (2010).
Wall, et al., "Biomimetic matrices for myocardial stabilization and stem cell transplantation", J Biomed Mater Res A 95(4), 1055-1066 (2010).
Wang, et al., ""Click" immobilizatoin of a VEGF-mimetic peptide on decellularized endothelial extracellular matrix to enhance angiogenesis", ACS Appl Mater Interfaces 6(11), 8401-8406 (2014).
Wang, et al., "Injectable cardiac tissue engineering for the treatment of myocardial infarction", J Cell Mol Med 14(5), 1044-1055 (2010).
Wang, et al., "Novel thermosensitive hydrogel injection inhibits post-infarct ventricle remodeling", Eur J Heart Fail 11 (1), 14-19 (2009).
Yamada, et al., "Induced pluripotent stem cell intervention rescues ventricular wall motion disparity, achieving biological cardiac resynchronization post-infarction", J Physiol 591(17), 4335-4349 (2013).

Yang, et al., "Human cardiovascular progenitor cells develop from a KDR plus embryonic-stem-cell-derived population", Nature 453(7194), 524-529 (2008).
Yao, et al., "Tissue kallikrein-modified human endothelial progenitor cell implantation improves cardiac function via enhanced activation of akt and increased angiogenesis", Lab Invest 93(5), 577-591 (2013).
Zhang, et al., "Cardiomyocyte grafting for cardiac repair: Graft cell death and anti-death strategies", J Mol Cell Cardiol 33(5), 907-921 (2001).
Zimmermann, et al., "Cardiac grafting of engineered heart tissue in syngenic rats", Circulation 106(12 Suppl 1), I151-I157 (2002).
Zimmermann, et al., "Cardiac tissue engineering: implications for pediatric heart surgery", Pediatr Cardiol 30(5), 716-723 (2009).
Annabi, et al., "Controlling the porosity and microarchitecture of hydrogels for tissue engineering", Tissue Eng Part B Rev 16(4), 371-383 (2010).
Annabi, et al., "Highly Elastic Micropatterned Hydrogel for Engineering Functional Cardiac Tissue", Adv Funct Mater 23(39), 4950-4959 (2013).
Banerjee, "Dynamic interactions between myocytes, fibroblasts, and extracellular matrix", Ann N.Y. Acad Sci 1080, 76-84 (2006).
Baxter, et al., "Adaptive changes in cardiac fibroblast morphology and collagen organization as a result of mechanical environment", Cell Biochem Biophys 51(1), 33-44 (2008).
Bearat, et al., "Comparison of properties between NIPAAm-based simultaneously physically and chemically gelling polymer systems for use in vivo", Acta Biomater 8(10), 3629-3642 (2012).
Bearat, et al., "Synthesis, Characterization and Properties of a Physically and Chemically Gelling Polymer System Using Poly(NIPAAm-co-HEMA-acrylate) and Poly(NIPAAm-co-cysteamine)", J Biomater Sci Polym Ed 22(10), 1299-1318 (2011).
Beltrami, et al., "Adult cardiac stem cells are multipotent and support myocardial regeneration", Cell 114(6), 763-776 (2003).
Bergmann, et al., "Evidence for Cardiomyocyte Renewal in Humans", Science 324(5923), 98-102 (2009).
Bersell, et al., "Neuregulin1/ErbB4 Signaling Induces Cardiomyocyte Proliferation and Repair of Heart Injury", Cell 138(2), 257-270 (2009).
Cai, et al., "Injectable hydrogels with in situ double network formation enhance retention of transplanted stem cells", Adv Funct Mater 25(9), 1344-1351 (2015).
Camelliti et al., "Spatially and temporally distinct expression of fibroblast connexins after sheep ventricular infarction", Cardiovasc Res 62(2), 415-425 (2004).
Carmelliti, et al., "Structural and functional characterisation of cardiac fibroblasts", Cardiovasc Res 65(1), 40-51 (2005).
Campa, et al., "Notch activates cell cycle reentry and progression in quiescent cardiomyocytes", J Cell Biol 183(1), 129-141 (2008).
Ceccaldi, et al., "Alginate scaffolds for mesenchymal stem cell cardiac therapy: influence of alginate composition", Cell Transplant 21(9), 1969-1984 (2012).
Chen, et al., "BMP10 is essential for maintaining cardiac growth during murine cardiogenesis", Development 131(9), 2219-2231 (2004).
Chen, et al., "Electrophysiological Challenges of Cell-Based Myocardial Repair", Circulation 120(24), 2496-2508 (2009).
Cheng, et al., "Poly(N-isopropylacrylamide-co-Poly(ethylene glycol))-acrylate simultaneously physically and chemically gelling polymer systems", J Appl Polym Sci 106(2), 1201-1207 (2007).
Chilton, et al., "Evidence of intercellular coupling between co-cultured adult rabbit ventricular myocytes and myofibroblasts", J Physiol 583(Pt 1), 225-236 (2007).
Christman, et al., "Biomaterials for the treatment of myocardial infarction", J Am Coll Cardiol 48(5), 907-913 (2006).
Christman, et al., "Fibrin glue alone and skeletal myoblasts in a fibrin scaffold preserve cardiac function after myocardial infarction", Tissue Eng 10(3-4), 403-409 (2004).
Christman, et al., "Injectable fibrin scaffold improves cell transplant survival, reduces infarct expansion, and induces neovasculature formation in ischemic myocardium", J Am Coll Cardiol 44(3), 654-660 (2004).

(56) References Cited

OTHER PUBLICATIONS

Cui, et al., "In vitro study of electroactive tetraaniline-containing thermosensitive hydrogels for cardiac tissue engineering", Biomacromolecules 15(4), 1115-1123 (2014).

Cui, et al., "New hydrolysis-dependent thermosensitive polymer for an injectable degradable system", Biomacromolecules 8(4), 1280-1286 (2007).

Cutts, et al., "Biomaterial approaches for stem cell-based myocardial tissue engineering", Biomark Insights 10(Suppl 1), 77-90 (2015).

Dai, et al., "Delivering stem cells to the heart in a collagen matrix reduces relocation of cells to other organs as assessed by nanoparticle technology", Regen Med 4(3), 387-395 (2009).

Davis, et al., "Injectable self-assembling peptide nanofibers create intramyocardial microenvironments for endothelial cells", Circulation 111(4), 442-450 (2005).

Elbert, et al., "Conjugate addition reactions combined with free-radical cross-linking for the design of materials for issue engineering", Biomacromolecules 2(2), 430-441 (2001).

Elliott, et al., "NKX2-5eGFPw hESCs for isolation of human cardiac progenitors and cardiomyocytes", Nat Methods 8(12), 1037-1040 (2011).

Ellman, "Tissue sulfhydryl groups", Arch Biochem Biophys 82(1), 70-77 (1959).

Eschenhagen, et al., "Engineering myocardial tissue", Circ Res 97(12), 1220-1231 (2005).

Evans, "Economic impact of mechanical cardiac assistance", Prog Cardiovasc Dis 43(1), 81-94 (2000).

Fernandes, et al., "Synthetic matrices to serve as niches for muscle cell transplantation", Cells Tissues Organs 195 (1-2), 48-59 (2012).

Freed, et al., "Advanced tools for tissue engineering: Scaffolds, bioreactors, and signaling", Tissue Eng 12(12), 3285-3305 (2006).

Fujimoto, et al., "Synthesis, characterization and therapeutic efficacy of a biodegradable, thermoresponsive hydrogel designed for application in chronic infarcted myocardium", Biomaterials 30(26), 4357-4368 (2009).

Genead, et al., "Islet-1 Cells Are Cardiac Progenitors Present During the Entire Lifespan: From the Embryonic Stage to Adulthood", Stem Cells Dev 19(10), 1601-1615 (2010).

Giraud, et al., "Cell therapies for heart function recovery: focus on myocardial tissue engineering and nanotechnologies", Cardiol Res Pract, Article ID 971614, 10 pages (2012).

Grego-Bessa, et al., "Notch signaling is essential for ventricular chamber development", Dev Cell 12(3), 415-429 (2007).

Hasan, et al., "Injectable hydrogels for cardiac tissue repair after myocardial infarction", Adv Sci 2(11), Article ID 1500122, 18 pages (2015).

Heffernan, et al., "Bioengineered scaffolds for 3D analysis of glioblastoma proliferation and invasion", Ann Biomed Eng 43(8), 1965-1977 (2014).

Heffernan, et al., "Temperature responsive hydrogels enable transient three-dimensional tumor cultures via rapid cell recovery", J Biomed Mater Res A 104(1), 17-25 (2016).

Henderson, et al., "In vivo evaluation of injectable thermosensitive polymer with time-dependent LCST", J Biomed Mater Res A 90(4), 1186-1197 (2009).

Hsieh, et al., "Evidence from a genetic fate-mapping study that stem cells refresh adult mammalian cardiomyocytes after injury", Nat Med 13(8), 970-974 (2007).

Huang, et al., "Injectable PLGA porous beads cellularized by hAFSCs for cellular cardiomyoplasty", Biomaterials 33 (16), 4069-4077 (2012).

Hunt, et al., "Hydrogels for tissue engineering and regenerative medicine", J Mater Chem B 2, 5319-5338 (2014).

Ieda, et al., "Cardiac Fibroblasts Regulate Myocardial Proliferation through beta 1 Integrin Signaling", Developmental Cell 16(2), 233-244 (2009).

Ifkovits, et al., "Injectable hydrogel properties influence infarct expansion and extent of postinfarction left ventricular remodeling in an ovine model", Proc Natl Acad Sci U S A 107(25), 11507-11512 (2010).

Iyer, et al., "Engineered cardiac tissues", Curr Opin Biotechnol 22(5), 706-714 (2011).

Jiang, et al., "Injection of a novel synthetic hydrogel preserves left ventricle function after myocardial infarction", J Biomed Mater Res A 90(2), 472-477 (2009).

Jongpaiboonkit, et al., "An adaptable hydrogel array format for 3-dimensional cell culture and analysis", Biomaterials 29(23), 3346-3356 (2008).

Kaneko, et al., "On-chip constructive cell-network study (I): contribution of cardiac fibroblasts to cardiomyocyte beating synchronization and community effect", J Nanobiotechnol 9, 21, 13 pages (2011).

\* cited by examiner

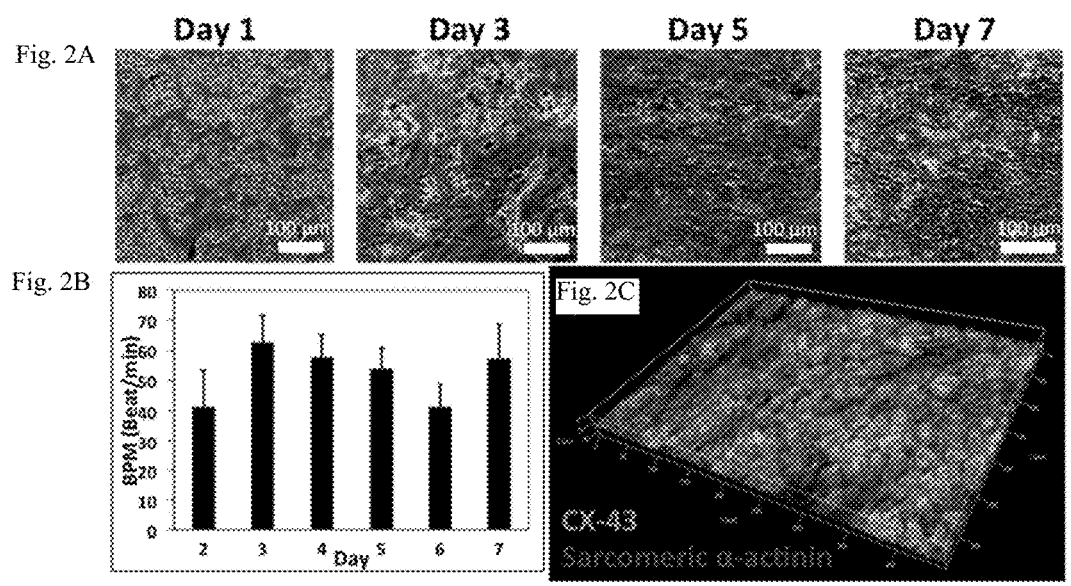

Fig. 7A
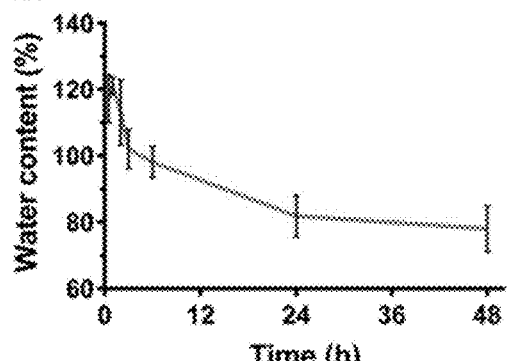
Fig. 7B
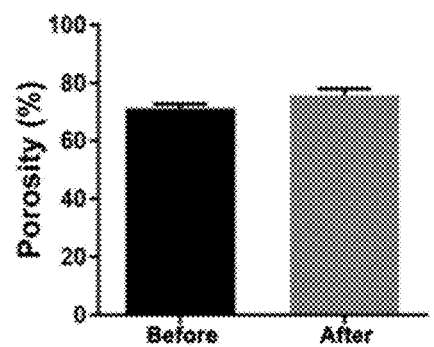
Fig. 7C Before hydration
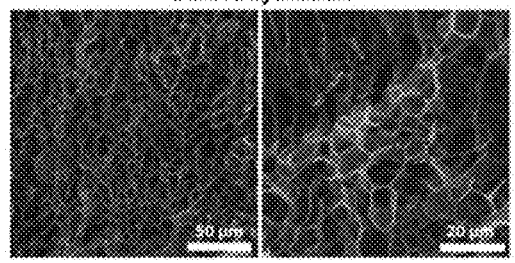
Fig. 7D After hydration
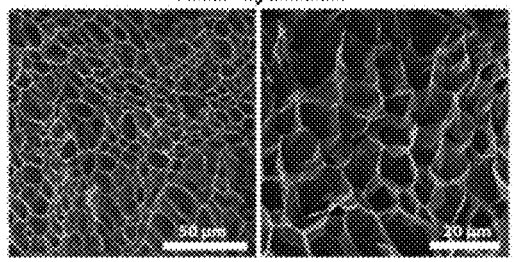
Fig. 7E
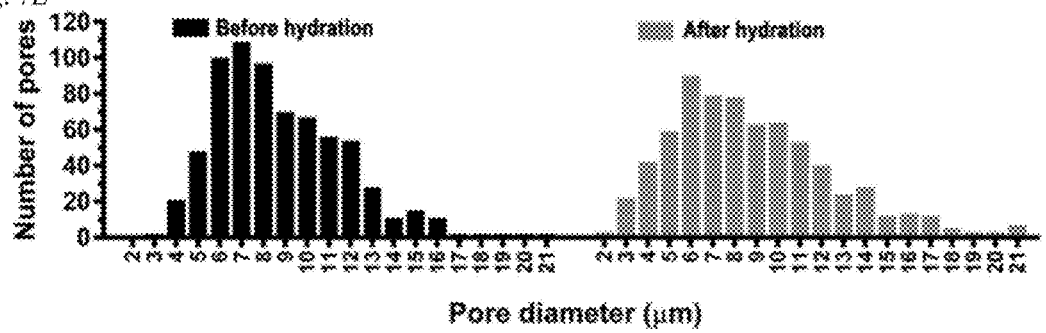

ized nations accounting for over 40% of all human death (He, J., et al. Archives of Internal Medicine. 2002; 162: 1619-1624; and Evans, R. W., et al. Progress in Cardiovascular Diseases. 2000; 43:81-94).

```
                             SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term methacrylic acid
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (11)..(11)
<223> OTHER INFORMATION: Lys(Ac)
<220> FEATURE:
<221> NAME/KEY: MOD_RES
<222> LOCATION: (13)..(13)
<223> OTHER INFORMATION: Lys(Ac)

<400> SEQUENCE: 1

Lys Leu Thr Trp Gln Glu Leu Tyr Gln Leu Lys Tyr Lys Gly Ile Cys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term methacrylic acid
<220> FEATURE:
<221> NAME/KEY: MOD_RES
<222> LOCATION: (1)..(1)
<223> OTHER INFORMATION: Lys(Ac)
<220> FEATURE:
<221> NAME/KEY: MOD_RES
<222> LOCATION: (11)..(11)
<223> OTHER INFORMATION: Lys(Ac)
<220> FEATURE:
<221> NAME/KEY: MOD_RES
<222> LOCATION: (13)..(13)
<223> OTHER INFORMATION: Lys(Ac)
```

```
<220> FEATURE:
<223> OTHER INFORMATION: C-term NH2

<400> SEQUENCE: 2

Lys Leu Thr Trp Gln Glu Leu Tyr Gln Leu Lys Tyr Lys Gly Ile
1               5                   10                  15
```

INJECTABLE CELL-LADEN BIOHYBRID HYDROGELS FOR CARDIAC REGENERATION AND RELATED APPLICATIONS

PRIORITY OF INVENTION

This application claims priority from U.S. Provisional Application Ser. No. 62/214,054, filed Sep. 3, 2015, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 20, 2016, is named 17555_032US1_SL.txt and is 1,404 bytes in size.

BACKGROUND

Cardiovascular diseases are among the prominent causes of morbidity and mortality in the developing and industrialized nations accounting for over 40% of all human death (He, J., et al. Archives of Internal Medicine. 2002; 162: 1619-1624; and Evans, R. W., et al. Progress in Cardiovascular Diseases. 2000; 43:81-94).

Ischemia-induced infarction can lead to 25% total cell loss within the ventricular myocardium in a short period of time and results in global remodeling and abnormal stress distribution through the myocardial tissue (Laflamme, M. A., et al. Nature. 2011; 473:326-35; and Tous E., et al. Journal of Cardiovascular Translational Research. 2011; 4:528-42). Due to the significantly limited self-regenerative capacity of the ventricular cardiomyocytes (CMs) within the adult mammalian heart (Bergmann, O., et al. Science. 2009; 324:98-102), myocardial infarction (MI) can ultimately lead to catastrophic heart failure (Segers, V. F. M., et al. Nature. 2008; 451:937-942). Heart transplantation at last stage is quite a prominent approach for treatment of heart failure; however it is crucially limited by inadequate donor supply and clinical complications associated with the transplantation process.

In the past few years, significant amount of efforts have been devoted to exploit efficient therapeutic strategies to induce long-term myocardial regeneration. These strategies span from stem cell transplantation to delivery of growth factors, gene, acellular scaffolds as well as engineered cell sheets and tissue constructs (Tous E., et al. Journal of Cardiovascular Translational Research. 2011; 4:528-42; Orlic, D., et al. Nature. 2001; 410:701-7055; Orlic, D., et al. Proceedings of the National Academy of Sciences of the United States of America. 2001; 98:10344-10349; Soonpaa, M. H., et al. Science. 1994; 264:98-101; Yamada, S., et al. Journal of Physiology-London. 2013; 591:4335-4349; Nelson, T. J., et al. Circulation. 2009; 120:408-416; Zimmermann, W. H., et al. Circulation. 2002; 106:I151-I157; Nugent, H. M., et al. Circulation Research. 2003; 92:1068-1078; Eschenhagen, T., et al. Circulation Research. 2005; 97:1220-1231; and Wang, H., et al. Journal of Cellular and Molecular Medicine. 2010; 14:1044-1055).

Stem cell based transplantation has been one of the well-respected approaches for cardiac repair (Segers, V. F. M., et al. Nature. 2008; 451:937-942), as incorporation of cardiac or stem cells within the infarcted region of myocardium replace dysfunctional CMs while initiating the regeneration process with minimum risk of unfavorable tissue remodeling (Segers, V. F. M., et al. Nature. 2008; 451:937-942). These transplantation procedures are also minimally invasive which provide an enormous potential for translation into clinical practice (Laflamme, M. A., et al. Nature. 2011; 473:326-35).

Despite significant progress, the success of stem cell based therapies has been notably hindered due to the high rate of cell loss, poor integration with the host tissue and the lack of control over cellular distribution upon transplantation (Zhang, M., et al. Journal of Molecular and Cellular Cardiology. 2001; 33:907-921). Attempts to overcome these problems using tissue engineering techniques have not been clinically adopted, both because of the surgically invasive procedures to implant the engineered tissues substitutes, and the lack of vascularity (Laflamme, M. A., et al. Nature. 2011; 473:326-35).

Due to the current limitations of stem cell based therapies and tissue engineering strategies, there is still an ever growing need for innovate approaches for cardiac regeneration and repair.

SUMMARY

The present invention provides an injectable micro-tissue system for functional regeneration of myocardium. The micro-tissue system of the present invention comprises a temperature-responsive dual-gelling hydrogel, which undergoes physical temperature-dependent gelation in situ to provide a cell scaffold, a vasculogenic moiety, such as QK-cys (methacrylic acid-K(Ac)LTWQELYQLK(Ac)YK (Ac)GI-C (SEQ ID NO: 1)), which promotes vascular formation within the micro tissue system, and micro-tissues formed from tissue-specific cells, preferably cardiac cells, which are embedded in the hydrogel. The hydrogel may also comprise endothelial cells to promote vascularization within the micro tissue system in situ.

Accordingly, one embodiment provides a temperature-responsive dual-gelling hydrogel comprising a plurality of hydrogel polymers and a polymer cross-linking moiety, wherein the lower critical solution temperature (LCST) of the hydrogel polymers is less than 37° C., and the polymer cross-linking moiety is capable of chemically cross linking to the hydrogel polymers to form a polymer matrix. Having an LCST of less than 37° C. means that the hydrogel polymers will undergo temperature driven gelation in situ within a subject (i.e. when exposed to a temperature of 37° C. or greater). In addition the hydrogel polymers will also undergo chemical cross-linking with the polymer cross-linking moiety. The dual gelling mechanism of the hydrogel of the present invention allows administration of the hydrogel with a biocompatible aqueous solvent (e.g. phosphate buffered saline, PBS) but allows the material to become a more hydrophobic chemically cross-linked material in situ.

In one embodiment, the temperature-responsive dual-gelling hydrogel further comprises a vasculogenic peptide, optionally a VEGF mimic peptide. The inclusion of a vasculogenic peptide promotes the formation of microcapillaries within the 3D microenvironment of the injected hydrogel and also facilitates the integration of the engineered vascularized network within the host vasculature. The vasculogenic peptide may be QK-cys (methacrylic acid-K(Ac)LTWQELYQLK(Ac)YK(Ac)GI-C (SEQ ID NO: 1)).

In one embodiment, the temperature-responsive dual-gelling hydrogel further comprises one or more engineered micro-tissues, preferably cardiac micro tissues. The engineered micro tissues are dispersed within the hydrogel and become embedded when the hydrogel undergoes gelation. The inclusion of micro-tissues within the hydrogel increases control over cell-cell and cell-matrix interactions which will improve cell survival in situ. The cardiac micro-tissues may be formed from various cardiac cell types.

In any of the embodiments described herein, the hydrogel may further comprise endothelial cells. The endothelial cells become embedded in the hydrogel on gelation and can promote vascularization, particularly in combination with the vasculogenic peptide.

In any of the embodiments described herein, the hydrogel polymers may comprise acrylate and the polymer cross-linking moiety may be thiolated gelatin. The thiolated gelatin undergoes a chemical cross-linking reaction with acrylate in the hydrogel polymers to chemically cross-link the hydrogel polymers. The acrylate is preferably provided by N-acryloylacrylamide (NAA).

One embodiment provides a hydrogel polymer comprising monomers of N-isopropylacrylamide (NIPAAm), R)-α-Acryloyloxy-β, β-dimethyl-γ-butyrolactone (DBLA), Jeffamine M-1000 acrylamide (JAAm) and N-acryloylacrylamide (NAA).

In one embodiment, the hydrogel polymer is poly(NIPAAm-co-DBLA-co-JAAm-co-NAA).

One embodiment provides a method for manufacturing harvestable micro-tissues for embedding within a hydrogel, the method comprising seeding one or more microwells with a cell culture solution and incubating the microwells under conditions suitable for the formation of micro-tissues. Preferably the cells are cardiac cells.

In one embodiment the invention provides a pre-hydrogel peptide comprising NIPAA, DBLA and NASI comonomers. Preferably the pre-hydrogel peptide is poly(NIPAA-co-DBLA-co-NASI).

In one embodiment the invention provides a method of manufacturing a pre-hydrogel peptide library comprising synthesizing a library of pre-hydrogel peptides comprising NIPAA, DBLA and NASI comonomers, wherein the pre-hydrogel peptides comprise from 64 to 100% NIPAAm, 0 to 6% DBLA and 0% to 30% NASI monomers.

In one embodiment the invention provides a hydrogel as described herein for use in therapy.

In one embodiment the invention provides a hydrogel as described herein for use in treating or preventing myocardial infarction.

BRIEF DESCRIPTION OF THE DRAWINGS

FIGS. 2A-2C. Preliminary results on Poly (NIPAAm-co-JAAm-co-HEMA-RGD) embedded cardiac cells. FIG. 2A. Phase contrast of CMs and CFs co-culture as a function of time at Day 1, 3, 5 and 7 (left to right). Scale bar represents 100 μm; FIG. 2B. CMs beating as a function of time. Y-axis=BPM" (beat/min)", X-axis=Day (2", 3", 4", 5", 6" or 7" respectively from left to right); FIG. 2C. Immunostaining for cardiac CX-43 and Sarcomeric Alpha Actinin FIG. 3A. Synthesis plan for Poly(NIPAAm-co-DBLA-co-JAAm-co-NASI). The result will be a polymer that when combined with multi thiol gelatin will exhibit dual physical and chemical cross-linking at 37° C.

FIG. 6D. Changes in storage modulus of the PNJ-Gelatin hybrid hydrogel according to the temperature increase from 25° C. (preparation temperature) to 37° C. (incubation temperature). G': storage modulus, G": loss modulus.

FIGS. 7A-7E. The physical characteristics of PNJ-Gelatin hydrogel. FIG. 7A. The change in the water content level (%) of the hydrogel during 48 h of hydration. FIG. 7B. The percent of void structure (porosity) (%), FIG. 7C. and FIG. 7D. Low and high magnification SEM micrographs showing macroporous architecture. FIG. 7E. Pore size distribution of lyophilized hydrogel before and after hydration (24 h).

FIG. 8A. The depth coding image (scale bar represents 100 μm) of encapsulated cardiac cells within PNJ-Gelatin hydrogel (top-view & cross-section) confirming the formation of a 3D tissue construct (day 1). FIG. 8B. The phase-contrast (scale bars represent 100 μm) and fluorescent images of mono- and co-culture groups illustrating cell morphology at days 1 and 7 of culture. Insets on phase-contrast (scale bars represent 50 μm) and stained images show the magnified images (inset #1 and 2 show CFs and CMs respectively; inset #3 and 4 display small protrusions in CMs). FIG. 8C. Quantified viability (%) of both mono- and co-cultured groups at days 1 and 7. (n=3; *p<0.05). (For interpretation of the references to color in this figure legend, the reader is referred to the web version of this article.)

FIG. 9A. F-actin fibers stained images in both culture groups representing the cytoskeleton organization at 20× and 40× magnifications; FFT images (inset) indicate fiber alignment within the formed 3D cardiac tissue. The magnified spots and related inset FFT images illustrate the local alignment of F-actin fibers. FIG. 9B. The average coverage area ($\mu m^2$) of the F-actin fibers at day 7 of culture (n>10; *p<0.05).

FIG. 11C and FIG. 11D represent beating signals of five different subsets (0.5×0.5 $mm^2$) within hydrogel sample (2.5×2.5 $mm^2$) at day 7. The quantified (FIG. 11E) amplitude and (FIG. 11F) frequency variations represented as indexes comparing the synchrony of beating for mono- and co-culture groups.

DETAILED DESCRIPTION OF THE INVENTION

Figure 1A:
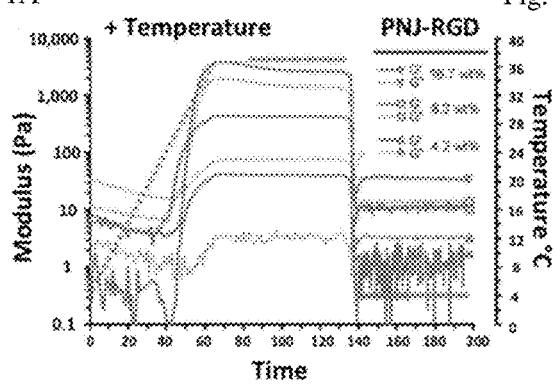
FIG. 1A. Poly(NIPAAm-co-JAAm-co-RGD) [90.7:8.8:1.1 NIPAAm:JAAm:RGD composition] showing temperature-responsive gelation at temperature between room temperature and body temperature.

Stem cell transplantation and tissue engineering strategies have tremendous potential for repair and/or regeneration of injured myocardium. However, due to the structural complexities of the native myocardium and the technical challenges associated with these strategies, functional regeneration of cardiac tissue in mammals has not yet been fully realized. The present inventors have developed an injectable micro-tissue system for functional regeneration of tissues, particularly the myocardium.

The micro tissue system of the present invention comprises a hydrogel which provides a cell scaffold, and cardiac cells which are embedded in the hydrogel. The hydrogel undergoes physical and chemical gelation upon administration to a subject. The hydrogel is bioresorbable, cures to provide final elastic modulus of 40-60 kPa and degrades within 2-3 weeks.

The hydrogel is formed from a plurality of hydrogel polymers which undergo gelation by physical temperature-dependent and chemical cross linking reactions. The hydrogel polymer contains any or all of the monomers NIPAAm, for temperature gelation, DBLA, for biodegradation, NAA, to provide a reactive site for chemical reaction in a Michael type addition reaction, and/or JAAm, to provide control of hydrogel water content independent of material LCST.

Following dual gelation the hydrogel may comprises a plurality of cross-linked hydrogel polymers, wherein the hydrogel polymers are cross-linked by a cross-lining moiety, a vasculogenic peptide, endothelial cells and cardiac microtissues, wherein the endothelial cells and cardiac microtissues are embedded within the hydrogel.

The term "acrylate" has the structure of:

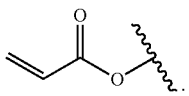 [SMILES: *OC(=O)C=C]

The acrylate group can typically be provided by N-acryloylacrylamide (NAA) or acryloyl chloride.

The composition of NIPAAm, DBLA, NAA, and JAAm monomers in the hydrogel will vary in line with the amount of NIPAA, DBLA and NASI in the pre-polymer as described herein.

The hydrogel polymer is a copolymer, preferably a tetrapolymer. Preferably the hydrogel polymer is a tetrapolymer of NIPAAm, DBLA, NAA, and JAAm monomers. The hydrogel polymer is preferably poly (NIPAAm-co-DBLA-co-JAAm-co-NAA).

A hydrogel polymer comprising these monomers has several advantages over known temperature-responsive polymers. The use of dimethyl-γ-butyrolactone acrylate (DBLA) as a comonomer provides degradation of the hydrogel without generation of free lactic acid. Furthermore, with the incorporation of side-chains of Jeffamine M-1000 (JAAm; a PEG-PPO copolymer), the present inventors have been able to adjust the swelling of the gel at 37° C. (reducing syneresis) nearly independent of the LCST. Finally, functionalization of the material with NASI substitute, to give N-acryloylacrylamide (NAA) side chain, has been shown to improve mechanical properties, when cross-linked with gelatin multi-thiol, and enables incorporation of a vasculogenic, VEGF mimic peptide covalently bond to the hydrogel. Thus, the present invention provides a new class of biomaterials with specifically tuned properties for the use as an injectable, in situ forming, and dual cross-linking cardiac cell embedded hydrogel.

In some aspects the hydrogel may contain a mixture of two or more different hydrogel polymers. Thus, in some aspects the hydrogel polymer may be a terpolymer and the hydrogel may contain a mixture of two or more different terpolymers.

In some aspects the hydrogel may comprise a terpolymer of NIPAAm, DBLA, and JAAm and a terpolymer of NIPAAm, DBLA, and NAA.

The hydrogel polymer has an LCST which is less than the average body temperature of the subject. The subject will generally be mammalian and the average body temperature of mammals is well known and is generally between about 37° C. and 40° C. The average body temperature of a human is about 37° C. Thus, the LCST is the hydrogel polymer is preferably less than 37° C.

LCST is the hydrogel polymer may be less than 37° C., 36° C., 35° C., 34° C., 33° C., 32° C., 31° C. or 30° C.

Having an LCST which is less than the average body temperature of the subject means that the hydrogel polymers will undergo temperature-dependent gelation in situ within the subject. Thus, upon administration to the subject, the hydrogel polymers initially undergo a physical gel transition as the temperature increases above the LCST to set the hydrogel in place.

Over time, in situ hydrolysis of monomers within the hydrogel polymer causes the LCST of the polymer to rise above the body temperature of a subject (i.e. above 37° C.). Thus, this time-dependent LCST means that the hydrogel is bioresorbable.

Preferably the hydrogel is bioresorbable within about 2-3 weeks. The hydrogel may be bioresorbable within about 4 weeks, within about 3 weeks or within about 2 weeks.

Preferably the hydrogel cures to provide final elastic modulus of 40-60 kPa. The final elastic modulus may be 30, 40, 50, 60, 70 kPa or any range selected from these limits.

Characteristics of the hydrogel such as the speed with which it is broken down in the body, the final elastic modulus can be altered by varying the composition of the copolymers within the hydrogel. For example, the rate of degradation can be varied by adjusting the amount of DBLA, hydrogel swelling can be varied by adjusting the amount of JAAm and mechanical properties can be varied by adjusting the composition of NAA in the polymer (which forms cross links to thiolated gelatin).

The hydrogel polymer is formed by one or more post polymerization modifications of a pre-hydrogel polymer.

The pre-hydrogel polymer may comprise or consists of NIPAA and/or DBLA and/or NASI monomers. The amount of each copolymer may be varied in order to tailor degradation times, elastic moduli (chemical cross-link densities), and water swelling in the hydrogel. Thus, in some aspects the pre-hydrogel polymer may contain from 0% to 30% NASI, 0 to 6% DBLA, and 64 to 100% NIPAAm.

The pre-hydrogel polymer is preferably poly(NIPAA-co-DBLA-co-NASI).

The post-polymerization modification may comprise functionalization of one or more monomers in the pre-hydrogel polymer. The post polymerization modification preferably results in the incorporation of side-chains into the polymer. The side chains may be N-acryloylacrylamide (NAA) and/or side chains of a PEG-PPO copolymer, such as Jeffamine M-1000 (JAAm).

The post-polymerization modification may be an amine reaction. In a preferred post-polymerization modification the NASI in each pre-hydrogel polymer is functionalized by amine reaction with the NASI monomer to provide acrylate functionality and JAAm content.

The hydrogel polymer is preferably poly(NIPAAm-co-DBLA-co-JAAm-co-NAA), wherein the hydrogel polymer may contain from 0% to 30% NAA, 0% to 30% JAAm, 0 to 6% DBLA, and 34 to 100% NIPAAm.

In one embodiment the invention provides a method of manufacturing a pre-hydrogel peptide library comprising synthesizing a library of pre-hydrogel peptides comprising NIPAA, DBLA and NASI comonomers, wherein the pre-hydrogel peptides comprise from 64 to 100% NIPAAm, 0 to 6% DBLA and 0% to 30% NASI monomers. In one aspect the invention provides a library of pre-hydrogel peptides each containing from 64 to 100% NIPAAm, 0 to 6% DBLA and 0% to 30% NASI monomers.

In one embodiment the hydrogel polymer comprises monomers of N-isopropylacrylamide (NIPAAm), Jeffamine M-1000 acrylamide (JAAm) and hydroxylethyl methacrylate (HEMA). The HEMA monomers comprise hydroxyl groups and at least one of the hydroxyl groups on the HEMA monomers is converted to an acrylate group.

In one embodiment the hydrogel polymer is poly(NIPAAm-co-JAAm-co-HEMA), wherein the hydrogel polymer may contain from 1% to 30% JAAm, 1 to 10% HEMA, and 60 to 98% NIPAAm. The HEMA monomers comprise hydroxyl groups and at least one of the hydroxyl groups on the HEMA monomers is converted to an acrylate group.

In one embodiment the hydrogel polymer is poly(NIPAAm-co-JAAm-co-HEMA-acrylate), wherein the hydrogel polymer may contain from 1% to 30% JAAm, 1 to 10% HEMA, and 60 to 98% NIPAAm.

In one embodiment the hydrogel polymer has a molecular weight from 2,000 to 100,000.

The hydrogel further comprises a polymer cross-linking moiety. The polymer cross-linking moiety chemically links the hydrogel polymers thereby providing a mechanically robust cell scaffold. The cross-linking reaction occurs after the initial temperature-dependent gelation and results in a polymer matrix, which has more resistance to creep and thus better integration into the tissue of interest (which is preferably the myocardium).

Preferably the chemical cross-linking moiety is capable of undergoing a Michael type addition reaction with the hydrogel polymers. The polymer cross-linking moiety is preferably gelatin, more preferably multi-thiolated gelatin. In this latter embodiment, a Michael type addition reaction occurs between acrylamide in the hydrogel polymers and thiols of multi-thiol gelatin.

In one embodiment the hydrogel polymer is poly(NIPAAm-co-JAAm-co-HEMA) and the polymer cross-linking moiety is thiolated gelatin, and wherein the HEMA monomers comprise hydroxyl groups and at least one of the hydroxyl groups on the HEMA monomers is converted to an acrylate group, and wherein the hydrogel polymer may contain from 1% to 30% JAAm, 1 to 10% HEMA, and 60 to 98% NIPAAm.

The presence of hydrogel polymers with an LCST, which is less than 37° C. and a polymer cross-linking moiety means that the hydrogel is capable of dual gelation by both physical temperature-driven, and chemical cross-linking mechanisms. For example, the hydrogel may undergo a Michael type addition reaction when the hydrogel is at 25° C. and dual gelation with both physical temperature driven physical gelation and Michael type addition chemical cross-linking at 37° C. Thus, the hydrogel is capable of dual gelation in-situ within a subject.

The hydrogel may further comprise a vasculogenic moiety. Vasculogenic moieties provide vasculogenic properties within the hydrogel. Vasculogenic moieties promote the formation of microcapillaries and facilitate the integration of the engineered vascularized network throughout the host vasculature.

Suitable vasculogenic moieties are known in the art. The vasculogenic moiety may be a peptide, for example a vasculogenic VEGF mimic peptide. Suitable vasculogenic VEGF mimic peptides include QK (methacrylic acid-K(Ac)LTWQELYQLK(Ac)YK(Ac)GI-NH$_2$ (SEQ ID NO: 2)) and QK-Cys (a covalently bound vasculogenic peptide) (methacrylic acid-K(Ac)LTWQELYQLK(Ac)YK(Ac)GI-C (SEQ ID NO: 1)).

The vasculogenic peptide is preferably conjugated to the hydrogel polymer. The vasculogenic peptide may be conjugated through a Michael type addition reaction between the peptide and the hydrogel polymers. Conjugation of the vasculogenic peptide provides vasculogenic activity within the hydrogel structure.

The vasculogenic peptide may be included in the hydrogel at a concentration of between 10-200 ug/ml, between 25 and 150 ug/ml, or at 25, 100 or 150 ug/ml.

In some embodiments the hydrogel further comprises cells. Preferably the cells are cardiomyocytes (CMs) and/or cardiac fibroblasts (FMs). In one embodiment the ratio of CMs to FMs is about 2:1.

The invention also provides a method for manufacturing a cell-laden temperature responsive dual-gelling hydrogel comprising:
  a) preparing a hydrogel polymer that comprises at least one acrylate group, wherein the LCST of the hydrogel polymer is less than 37° C.;
  b) mixing the hydrogel polymer with cells;
  c) adding a polymer cross-linking moiety to the mixture of hydrogel polymer and cells.

In one embodiment the method further comprises incubating the mixture of the hydrogel polymer, the cells and the polymer cross-linking moiety at 37° C. or above 37° C.

In one embodiment, the hydrogel polymer is poly(NIPAAm-co-JAAm-co-HEMA), and wherein the HEMA monomers comprise hydroxyl groups and at least one of the hydroxyl groups on the HEMA monomers is converted to an acrylate group.

In one embodiment the polymer cross-linking moiety is thiolated gelatin.

In one embodiment the cells are CMs and/or FMs. Preferably, the ratio of CMs to FMs is about 2:1.

In some embodiments the hydrogel further comprises engineered micro tissues. Micro tissues are engineered tissues, which are formed from tissue-specific cells which have a well-defined architecture and aim to mimic the native cell composition of the tissue of interest. The micro tissues may comprise one or more cell types, or may comprise one cell type. The micro tissues are formed from cells which are located in the tissue of interest. Preferably the micro tissue is cardiac tissue formed from cardiac cells.

The micro tissues can be administered to the site of injured tissue and then retained with the in situ-forming hydrogel. Preferably the micro tissues are administered in conjunction with the hydrogel and are then encapsulated within the hydrogel upon gelation in situ. Without being bound by theory it is believed that the formation of micro-tissues will promote cellular communication, which ultimately leads to enhanced cell survival upon transplantation of the tissues into a subject.

The micro tissues are generally three dimensional reflecting the shape of the container or mold in which they were cultured. Preferably the micro tissues are approximately spherical in shape. The micro-tissues may be about 20 µm, 30 µm, 40 µm, 50 µm, 75 µm or 100 µm in diameter (or any range selected from these sizes).

The micro-tissues may be manufactured by a method comprising seeding one or more microwells with a cell culture solution and incubating the microwells under conditions suitable for the development of micro-tissues. Conditions suitable for the development of micro-tissues include incubating the cell culture at a temperature suitable for tissue formation. Generally incubation will be at about 37° C.

The hydrogel may further comprise one or more additional cell types which are dispersed within the hydrogel. The cells may be endothelial cells and/or pericyte cells, preferably endothelial cells. The inclusion of additional cell types such as endothelial cells may enhance angiogenesis, particularly in the presence of a vasculogenic peptide. When the hydrogel has undergone physical temperature-dependent and optionally also chemical gelation then the cells are encapsulated within the hydrogel.

The one or more additional cell types may be encapsulated within the hydrogel at a density of $5-20\times10^5$ cells/ml, or a density of about $5-10\times10^5$ cells/ml.

The one or more additional cell types may be co-cultured with the micro-tissues within the hydrogel prior to administration to a subject.

A hydrogel as described herein preferably contains encapsulated cardiomyocytes micro tissues as well as human endothelial cells (ECs). Without being bound by theory it is believed that the encapsulation of endothelial cells and cardiac micro-tissues within the hydrogel will provide a survival advantage on cardiac micro-tissues in vivo. For example when the cells are subjected to a tense microenvironment (i.e. increased stress, hypoxia) upon myocardial infarction.

The hydrogel of the present invention requires a minimally invasive procedure, since it can be delivered via catheter within the infarcted zone of myocardium. Therefore, the proposed approach provides a significant potential for translation into clinical practice and personalized therapy. Thus, one embodiment provides a hydrogel as described herein for use in therapy.

One embodiment provides a hydrogel as described herein for delivering cells to an infarct region in a mammal in need of such treatment.

One embodiment provides a hydrogel as described herein for use in treating heart disease, wherein the heart disease is a myocardial infarction. The hydrogel may be used for preventing the reassurance of a disease, for example heart disease.

A hydrogel as described herein may be administered to a subject. Preferably the subject is a mammalian subject such as a human, a pig, non-human primate, rat or mouse. Most preferably the subject is human.

The hydrogel and micro-tissue are administered to the tissue of interest within a subject. Preferably the tissue is injured myocardium, for example tissue within the infarcted zone of myocardium. The hydrogel may be administered by injection into a subject in need thereof in order to minimize the use of surgically invasive procedures, for example the hydrogel can be injected within the site of injured myocardium. The hydrogel can be delivered via a catheter.

The present invention may involve the use of pharmaceutical compositions, which comprise a hydrogel as described herein for delivery into a subject. The hydrogel will ideally be administered with biocompatible aqueous solvent. Suitable biocompatible aqueous solvents are known in the art. The biocompatible aqueous solvent may be PBS. The hydrogel may be formulated into a pharmaceutically acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

Development of Injectable NIPAAm-Based Hydrogels for Cardiac Tissue Engineering

A temperature-responsive injectable hydrogel for cardiac tissue engineering was developed. In particular, poly(NIPAAm-co-JAAm-co-HEMA-RGD) (pNJ-RGD) (HEMA: Hydroxyethylmethacrylate) was synthesized for the co-culture of CMs and CFs.

Figure 1B:
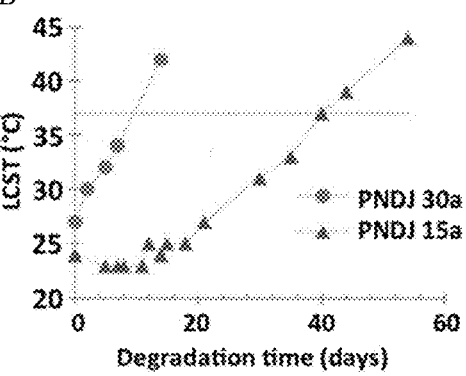
FIG. 1B. Degradation kinetics of poly(NIIPAAm-co-DBLA-co-JAAm) hydrogels at 5 wt % (PBS, pH 7.4). Increased JAAm content resulted in higher initial LCST and faster degradation.

The precursor polymer poly(NIPAAm-co-JAAm-co-HEMA) was synthesized by free radical polymerization of NIPAAm, JAAm, and HEMA monomers in anhydrous benzene initiated by Azobisisobutyronitrile (AIBN). After initiation, the reaction proceeded at 65° C. under nitrogen for 18 hr. An equal volume of acetone was added to re-dissolve the polymer, which was then precipitated in cold diethyl ether, collected by filtration, and vacuum dried overnight. Poly(NIPAAm-co-JAAm-co-HEMA) was then reacted with acryloyl chloride to give pendent acrylates in a reaction similar to that reported previously (Vintersten, K., et al. Genesis. 2004; 40:241-246). Poly(NIPAAm-co-JAAm-co-HEMA-RGD) or pNJ-RGD was formed by Michael addition of a peptide containing a reactive thiol and an RGD sequence onto the acrylates of the polymer. The polymer was purified by dialysis in deionized water at 3500 MWCO for 1 week and lyophilized to obtain the RGD-modified hydrogel. These materials were characterized and were shown to possess temperature-responsive gelation (FIG. 1A) and bioresorbable properties due to time-dependent LCST (FIG. 1B) (Wang, L., et al. ACS Appl Mater Interfaces. 2014; 6:8401-8406).

CMs and CFs (1:1 ratio) obtained from 2 day old neonatal rat (Heffernan, J. M., et al. Annals of Biomedical Engineering. 2014; and Cui, Z. W., et al. Biomacromolecules. 2007; 8:1280-1286) were encapsulated within the pNJ-RGD hydrogel with a total cell density of $25\times10^6$/ml of hydrogel solution. Cellular viability was calculated to be around 80±9.45%. From day 1 of culture, the co-culture the cells showed enhanced spreading and connectivity within the hydrogel matrix (FIG. 2A). The cells started beating in a synchronous fashion by day 2 of culture, in which the bating pattern was continued beyond day 7 (FIG. 2B). Particularly, cellular beating was found to be maximum at 62 beats/min on day 3 (FIG. 2C). Furthermore, expression of cardiac specific markers including sarcomeric α-actinin and connexin-43 was investigated. These markers play a crucial role in synchronized contraction of engineered cardiac tissues. Sarcomeric α-actinin and connexin 43 were well expressed throughout the construct confirming that pNJ-RGD hydrogel provide a suitable microenvironment to support cardiac cells functions.

Synthesis and Characterization of Injectable, Dual Cross-Linking, Bio-Hybrid Hydrogels Based on Copolymers of N-Isopropylacrylamide, Gelatin, and Vasculogenic Peptides for Use in Cardiac Regeneration A library of polymers with varying compositions of NIPAAm (for temperature gelation), DBLA (for biodegradation), NAA (reactive site for chemical reaction in a Michael type addition reaction), and JAAm (to provide control of hydrogel water content independent of material LCST) is generated in order to understand the structure property relationships for these materials.

Relationship of the composition to the properties of the polymer and to the properties of gels made with these materials when combined with multi-thiol gelatin (for chemical-crosslinking) and a vasculogenic VEGF mimic peptide (Wang, L., et al. ACS Appl Mater Interfaces. 2014; 6:8401-8406), QK-Cys (covalently bound vasculogenic peptide) (methacrylic acid-K(Ac)LTWQELYQLK(Ac)YK(Ac)GI-C (SEQ ID NO: 1)) is studied. The library is then used to rationally design a composition that provides physical gelation upon injection (at 37° C.), cures to provide final elastic modulus of 40-60 kPa, maintains volume of injection, and degrades in 2-3 weeks.

Jeffamine M-1000 Acrylamide (JAAm) Synthesis

JAAm is synthesized from Jeffamine M-1000 polyetheramine by acryloylation with acryloyl chloride. Jeffamine M-1000 (20 g, 20 mmol) is dissolved at 10 w/v % in dichloromethane (DCM) along with triethylamine (3.3 mL, 24 mmol) and maintained at 0° C. under nitrogen atmosphere. Acryloyl chloride (1.95 mL, 24 mmol) is then be added dropwise into the solution under stirring and the reaction is allowed to proceed for 1 hr at 0° C. and then at room temperature for at least 5 hr under nitrogen atmosphere. Following the reaction, DCM is evaporated and the remaining residue dissolved in 100 mM $NaHCO_3$. The product is extracted into DCM and the organic phase purified by column chromatography. JAAm is then vacuum dried overnight, then collected and stored at −20° C. until use.

Gelatin Thiol Synthesis (Heffernan, J. M, et al. Annals of Biomedical Engineering. 2014)

Dithiopropionic dihydrazide (DTP) is synthesized from 3,3 Dithiopropionic acid (DPA) and hydrazine hydrate. Free DPA (5 g) is dissolved in dry ethanol (50 mL) containing 1 to 3 drops of $H_2SO_4$ and refluxed under nitrogen for 1 hr. The reaction is concentrated under vacuum to less than 20 mL and then transferred to a separatory funnel with 60 mL diethyl ether. The organic layer is washed twice with 30 mL water and dried under vacuum. Gelatin (20 g) is dissolved in 2.0 L of water, and then DTP (20 g) is added dropwise while stirring. The pH of the reaction is adjusted to 4.75 with 1.0 M HCl and 1-Ethyl-3-[3-(dimethyl-lamino)propyl]carbodiimide (EDCl, 10 g) is added. The reaction is stopped by adjusting the pH to 7.0 with 1.0 M NaOH. Dithiolthreitol (DTT, 100 g) is added and the pH of the solution further adjusted to 8.5 with 1.0 M NaOH. After stirring for 24 hr at room temperature, the reaction pH is adjusted to 3.5 with 1.0 M HCl. The product is dialyzed (MWCO 3500) against 0.3 mM HCl containing 100 mM NaCl followed by dialysis against 0.3 mM HCl without salt (all at pH 3.5). After centrifugation the supernatant is lyophilized. Purity of the gelatin thiol is determined by GPC and H NMR and the degree of substitution is determined by H NMR and Ellman's test.

Polymer Synthesis

Figure 3A:
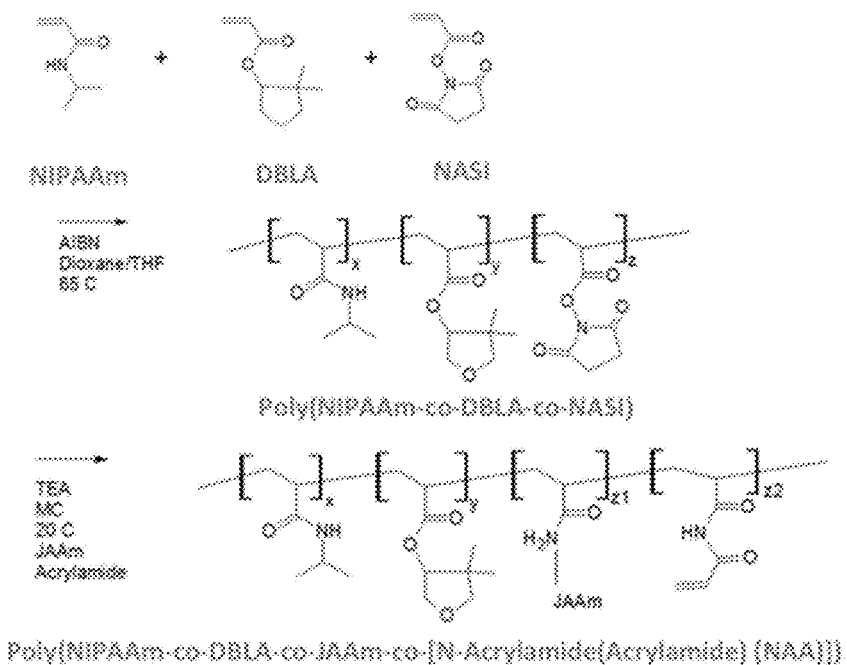
FIG. 3B. ternary composition diagram. Initial composition for the library Poly(NIPAAm-co-DBLA-co-JAAm-co-NASI) will be the hatched area in the lower right corner of this figure. Our preliminary work suggests that polymers with appropriate properties will be in these compositions.
Figure 3B:
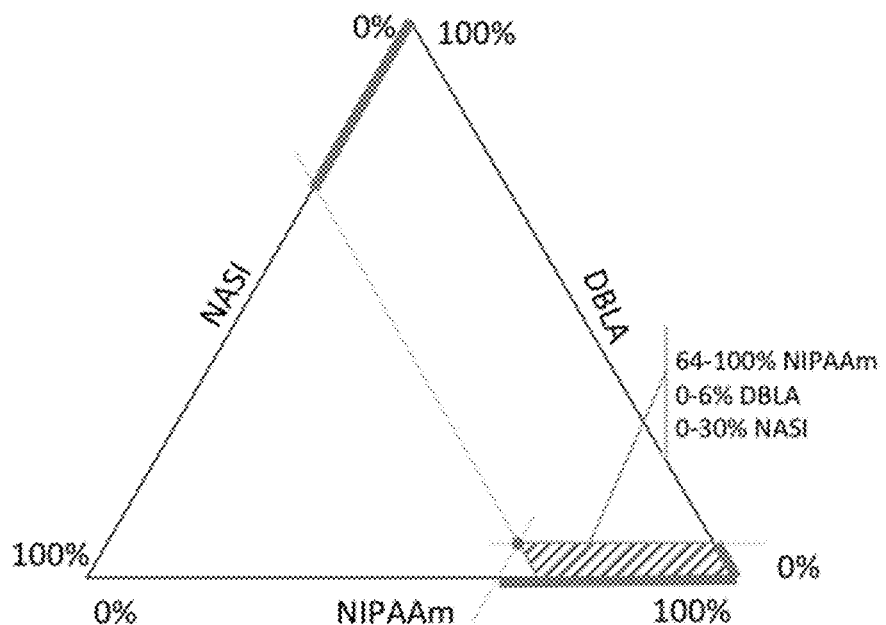

Copolymers of NIPAAm, (R)-α-Acryloyloxy-β,β-dimethyl-γ-butyrolactone (DBLA), and NASI (to later substitute with acrylamide and JAAm) are synthesized by free radical polymerization in 80% dioxane/20% THF as the solvent. FIG. 3A shows the synthesis plan for the copolymers. Molecular weight of the final product can be modified by adjustment of the dioxane/THF ratio. The given blend has given molecular weights near 40 kDa for preliminary poly (NIPAAm-co-DBLA-co-JAAm) polymerizations reported (Overstreet, D. J., et al. J Biomed Mater Res Part A. 2012; 101:1437-1446). Varying the ratios of the DBLA and NASI to the NIPAAm provide a library of materials with tunable degradation times, elastic moduli (chemical cross-link densities), and water swelling.

Initial work is focused on compositions in the hatched area. These are NASI contents from 0 to 30 mol %, DBLA contents from 0 to 6 mol % and the remainder NIPAAm. Previous work for these monomers combined with NIPAAm provide beginning ranges for NIPAAm combined with DBLA (Cui, Z. W., et al. Biomacromolecules. 2007; 8:1280-1286), HEMA (Lee, B. H., et al. Biomacromolecules. 2006; 7:2059-2064; Robb, S. A., et al. Biomacromolecules. 2007; 8:2294-2300; Cheng, V., et al. Journal of Applied Polymer Science. 2007; 106:1201-1207; Bearat, H. H., et al. Acta Biomaterialia. 2012; 8:3629-3642; and Bearat, H. H., et al. Journal of Biomaterials Science-Polymer Edition. 2011; 22:1299-1318), and JAAm (Overstreet, D. J., et al. Soft Materials. 2013; 11:294-304) that provide reasonable properties independently in approximately these relative compositions. Further work has shown polymers with pairs of these comonomers with NIPAAm providing reasonable properties; including DBLA/JAAm (Overstreet, D. J., et al. J Biomed Mater Res Part A. 2012; 101:1437-1446) that resulted in a bioresorbable NIPAAm with little syneresis (controlled volume swelling) and HEMA acrylate/JAAm that resulted in a cell scaffold that successfully supported culture of multiple cell types including glioblastoma cells when the HEMA acrylate is functionalized with RGD.

In post-polymerization modification, the NASI in each polymer is functionalized to provide acrylate functionality and JAAm content (Lee, B. H., et al. Biomacromolecules. 2006; 7:2059-2064; Robb, S. A., et al. Biomacromolecules. 2007; 8:2294-2300; Cheng, V., et al. Journal of Applied Polymer Science. 2007; 106:1201-1207; Bearat, H. H., et al. Acta Biomaterialia. 2012; 8:3629-3642; and Bearat, H. H., et al. Journal of Biomaterials Science-Polymer Edition. 2011; 22:1299-1318) by amine reaction with the NASI. Briefly, poly(NIPAAm-co-DBLA-co-NASI) is dissolved in methylene chloride. Triethylamine is then added. JAAm and acrylamide, dissolved in Methylene Chloride, are added to the polymer solution drop-wise while stirring. The reaction is allowed to continue at 20° C. for 24 hr. Unreacted NASI is converted to NIPAAm with addition of 50× excess of N-isopropylamine. Finally, the polymer is precipitated in diethyl ether, filtered, and vacuum-dried. The polymer is dialyzed in 5 mM HCl (the acid protects the DBLA from degradation) against 5 mM HCl at 5° C. exhaustively (3400 MWCO). The library created of these materials is used to elucidate the behavior of acrylamide functional NIPAAm with DBLA and JAAm to provide polymers with designed degradation times, dual physical/chemical cross-linking, and controlled swelling.

Characterization of the Mechanical, Structural, and Biological Properties of the Developed Hydrogels.

Polymer Characterization

1H-NMR spectroscopy (Varian Inova, 400 MHz) is used to determine the chemical composition of each polymer batch. Molecular weight and polydispersity is determined for each batch using GPC (Shimadzu Corp.) in conjunction with static light scattering (MiniDawn, Wyatt Tech. Corp.) in THF. Initial LCST in PBS (pH 7.4) is evaluated by cloud point determination (Parameters: 0.1 wt %, λ=450 nm), differential scanning calorimetry (MC-DSC, calorimetry Sciences Corp.) (Parameters: 5 wt %, heating 10-80° C.@1° C./min), and rheometry (MCR-101, Anton-Paar) (Parameters: 30 wt %, heating 10-60° C.@2° C./min, oscillatory 1% strain applied at 1 Hz, with normal force control). Lyophilized polymers are sterilized by ethylene oxide gas prior to in vivo work. Solutions for animal experiments are prepared by dissolving the lyophilized, sterilized polymer at 30 w/v % in sterile 150 mM PBS (pH 7.4) and used immediately upon dissolution.

In Vitro Gelation, Swelling and Degradation

Five-wt % to 30-wt % solutions of poly(NIPAAm-co-DBLA-co-JAAm-co-NAA) with varying comonomer contents in 0.1M PBS are prepared and adjusted to pH 7.4 with 1 N NaOH. These polymer samples are mixed with varying volumes of 0.5 to 3% solutions of thiolated gelatin/QK-Cys (methacrylic acid-K(Ac)LTWQELYQLK(Ac)YK(Ac)GI-C (SEQ ID NO: 1)). (with varying ratios of gelatin to QK-cys; the multi-thiol gelatin chemically cross-links the hydrogel, while QK-Cys provides vasculogenic properties within the hydrogel). The samples are placed at 25° C. or 37° C. This allows the material to gel by Michael type addition reaction alone at 25° C. and dual gelation with physical temperature driven physical gelation and Michael type addition chemical cross-linking at 37° C. After gelation and equilibrium all samples are brought to 37° C. and 2 mL of 37° C. prewarmed 0.1M PBS is added. Immediately and then at 1 day, 2 days, 1 wk, 2 wks, 1 month, 2 months, etc., the excess water is removed and the vial/gel weighed and the removed water is weighed. The degree of swelling is defined as $q=100(W-Wo)/Wo$; where W is the weight of the swollen gel, and Wo is the weight of the dried polymer. The concentration of polymer in the removed supernatant is determined by UV/Vis spectroscopy. Calibration curves are prepared by scanning UV absorbance versus concentration. Independent samples are used for each time period. The data expected from the in vitro gelation/swelling and degradation are the weight of the swollen polymer, the weight of the dried polymer, the weight of the water removed and the concentration of the polymer in the supernatant. This data is collected for a minimum of 3 samples for each material. This data is used to calculate the degree of syneresis (volume of water expelled), the equilibrium swelling, and mass loss versus time. This data is then compared to the results of the DSC and cloud point data to establish correlations between the transitions in LCST with mass loss. Quantification of the elastic or storage modulus (G' and G") for these materials is investigated using rheometry. To accomplish this work, 150 uL of polymer/gelatin/QK-cys (methacrylic acid-K(Ac)LTWQELYQLK(Ac)YK(Ac)GI-C (SEQ ID NO: 1)) solutions (prepared as described in the swelling study) are placed between the flat plates of a rheometer and at various (especially 25° C. and 37° C.) temperatures; the solutions/gels are subjected to oscillatory strain of fixed amplitude. This gives viscosity information for the sol states and elastic information of the gel states. Stress to shear failure is also investigated by increasing the stress amplitude with time until failure of the gel. Frequency and amplitude dependence of the shear properties is investigated by sweeping frequency and amplitude in independent experiments. Triplicate samples are performed and the mean and deviation determined for each synthesized polymer batch.

Expected Results and Alternatives

Dual gelling materials that cross-link by temperature driven physical interactions and simultaneous Michael type addition reaction between the acrylamide and thiols of multi-thiol gelatin are provided. This provides a mechanically robust cell scaffold that can be injected. QK-cys (methacrylic acid-K(Ac)LTWQELYQLK(Ac)YK(Ac)GI-C (SEQ ID NO: 1)) also conjugated through a Michael type addition reaction provides vasculogenic activity within the hydrogel structure. One challenge that may arise is the preparation of these 4 component polymers (tetrapolymers) including NIPAAm, DBLA, JAAm and NAA. The higher the complexity of the polymer structure, the difficult to produce reproducibly. The polymer synthesis itself is a terpolymer (3 monomers) with one of the monomers undergoing post polymerization modification to give the 4 distinct components in the final polymer. Therefore, the synthesis is expected to be successfully due to the reduce complexity during polymer synthesis. Polymers with 3 monomers, terpolymers (i.e. NIPAAm, DBLA, and JAAm in one polymer and NIPAAm, JAAm, and HEMA Acrylate [HEMA Acrylate is similar to NAA] in another polymer) have already been successfully prepared. With successful post polymerization modification, the tetrapolymer should be feasible. However, if the 4 component structure cannot be consistently generated, an alternative is to prepare two terpolymers: 1 with NIPAAm, DBLA, and JAAm and 1 with NIPAAm, DBLA and NAA and create gels using admixtures of these polymers mixed with multi-thiol gelatin/QK-cys (methacrylic acid-K(Ac)LTWQELYQLK(Ac)YK(Ac)GI-C (SEQ ID NO: 1)) to approximate a similar hydrogel system. The top bio-hybrid hydrogel candidates with 50-100% strain to failure rate and 2 weeks of degradation period is used for in vitro analysis as described below.

Micro Fabrication of Injectable Cardiac Micro-Tissues and Assessment of In Vitro Functionalities of the Cell-Embedded Bio-Hybrid Hydrogels The native myocardial architecture embodies highly organized and complex cellular constructs, with a dense network of capillaries packed in ECM proteins (Iyer, R. K., et al. Current Opinion in Biotechnology. 2011; 22:706-714). Such unique architecture is directly linked to the proper functioning of myocardium in vivo. Nevertheless, efficient heart regeneration heavily relies on numerous factors including proper cell sources, scaffolding biomaterials and vascularization (Vunjak-Novakovic, G., et al. Tissue Engineering Part B-Reviews. 2010; 16:169-187). Stem cell based transplantation is a well-respected therapeutic strategy for myocardial regeneration (Laflamme, M. A., et al. Nature. 2011; 473:326-35; and Segers, V. F. M., et al. Nature. 2008; 451:937-942). Unfortunately this approach does not regain fundamental complexities associated with the native myocardium. Furthermore, in most scenarios, this technique suffers from poor cellular retention and survival. Nevertheless, directed cell-cell and cell-matrix interactions plays a significant role in cellular behavior and function (Leri, A., et al. Current Problems in Cardiology. 2008; 33:91-153). Microengineered harvestable tissues using cardiomyocytes cells are developed, which can be embedded within the synthesized hybrid hydrogel. Extensive in vitro characterization is performed to test cellular survival, vascular formation as well as tissue contraction.

Generation of Cardiac Micro-Tissues

Figure 4:
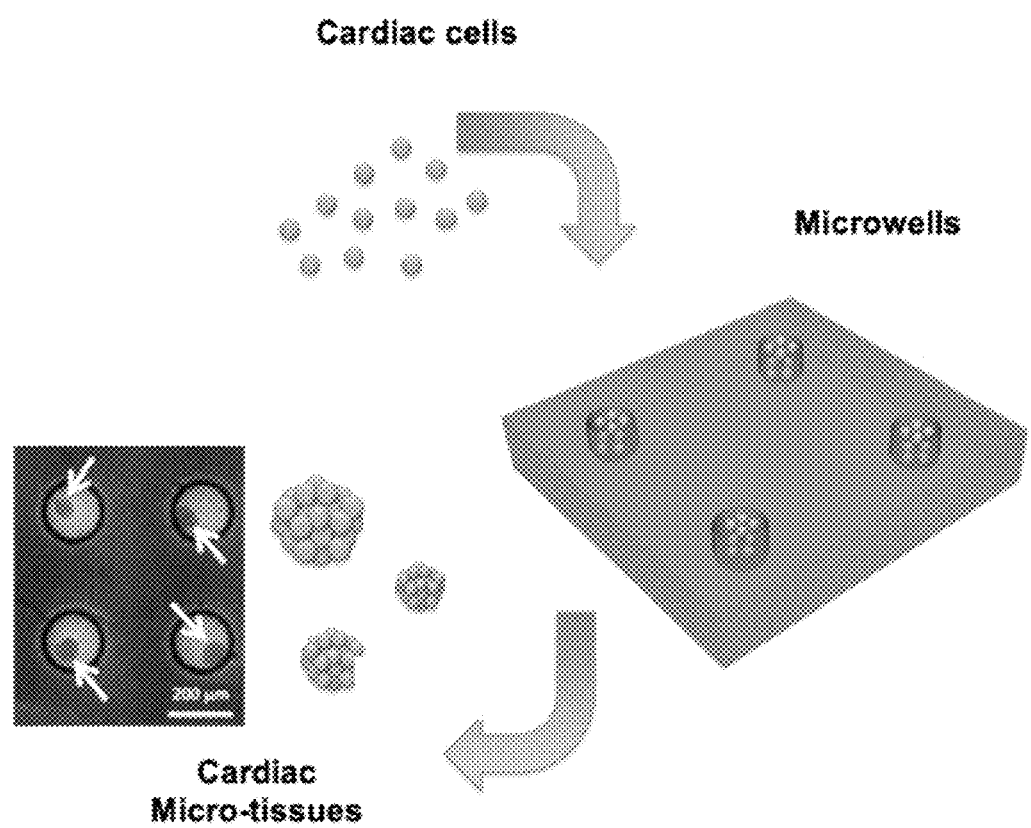
FIG. 4. Formation of cardiac micro-tissues using microwells.

Standard microwells are used to systematically engineer cardiac micro-tissues. Cardiomyocytes will be seeded in the microwells with the density of $10\times10^6$ cells/ml of cell culture solution. Passive cell seeding is expected to control cell capturing and the formation of cellular clusters within each microwells as demonstrated by our previous work (Nikkhah, M., et al. Ieee Sensors Journal. 2013; 13:1125-1132). Upon cell seeding, the microwells are rinsed in PBS to remove the excess cells from the top surfaces of the chip. Microwells are then placed inside 37° C. incubator for 3 days for the formation micro-tissues (FIG. 4). Each micro-tissue is an independent entity where cardiac cells can interact with each other and the surrounding hybrid hydrogel. After 1, 3, 5, 7, 14 days of culture, micro-tissues are harvested through gentle flow of PBS over the microwells and Live/Dead Assay Kit are used to quantify cell viability at the desired culture time point.

Encapsulation of Cardiac Micro-Tissues and ECs Within the Bio-Hybrid Hydrogels

The micro-tissues as well as human ECs are encapsulated within the top three top hydrogel candidates synthesized as described above. The following experimental groups are investigated in a systematic manner to characterize the in vitro functionalities the developed micro-tissues: (a) Controlled vascularization experiment using ECs encapsulated within the hybrid hydrogels; (b) Co-culture of micro-tissues along with ECs within the hybrid hydrogels.

(a) GFP expressing HUVECs (Lonza) are encapsulated with the density of $5-10\times10^5$ cells/ml within the three top hybrid hydrogel candidates. A cell encapsulated hydrogel droplet is injected on a TMSPMA functionalized glass slide using a standard 30 G needle. The cell-encapsulated solutions (~50-100 μl) are placed inside incubator for subsequent crosslinking. All of the experiments are performed in physiological conditions (37° C., 5% $CO_2$) in ECs specific culture media (EGM-2 bullet kit). After 1, 3, 5 and 7 days of culture, actin cytoskeleton is stained using Alexa fluor 595 phalloidin. Fluorescence images are taken using different filter sets to visualize GFP expressing HUVECs. Immunohistochemistry (IHC) analysis is also performed to study the expression of HUVECs (CD31, VE-cadherin) markers Additionally, the cells nuclei are stained using DAPI to assess the cellular organization and alignment using NIH ImageJ software within the hydrogel construct. Also, the sprouting densities of self-assembled microcapillaries throughout the hydrogel layers is investigated. The length of tubules, number of branches and diameter of lumens as indicators of capillary formation are measured. Furthermore, laminin and fibronectin, as angiogenic markers (Moon, J. J., et al. Tissue Engineering Part A. 2009; 15:579-585), are stained to define the effect of hybrid hydrogels on the expression of angiogenic marker. Mouse anti-fibronectin, mouse anti-laminin primary antibodies and Alexafluor 569 conjugated goat anti-mouse and Alexafluor 350 conjugated goat anti-mouse secondary antibodies, are used for this experiment within different sets of samples. Upon staining, confocal images at 5 different locations (40× or 63×) are used to define the fluorescent pixel intensity of the stained laminin and fibronectin. Overall, the controlled vascularization experiments (condition a) lead to the selection of the optimized ECs density as well as QK peptide (methacrylic acid-K(Ac)LTWQELYQLK(Ac)YK(Ac)GI-$NH_2$ (SEQ ID NO: 2)) concentration (25, 100 and 150 μg/ml).

(b) The cardiac micro-tissues are harvested from the responsive microwells and the hybrid hydrogel prepolymer solutions containing ECs are flown over the microwells to encapsulate the micro-tissues. For these experiments 50 μm, 75 μm and 100 μm (diameter) spherical shape micro-tissues are used. 250-400 micro-tissues are harvested from a single chip. The EC and cardiac micro-tissues are flown through a 30 G needle on a TMSPMA functionalized glass slide and placed inside 37° C. incubator for subsequent crosslinking. All the experiment are performed in 50% EC specific (Lonza) and 50% cardiac specific media. Using the library of the hybrid hydrogels developed as described above, the detailed effects of material properties, including the mechanical stiffness as well as the architecture of the hybrid hydrogels such as porosity on cell survival and functionalities are studied. Without being bound by theory, it is envisioned that the encapsulation of ECs and cardiac micro-tissues within the hybrid hydrogel provide a survival advantage on cardiac micro-tissues when the cells are subjected to tense microenvironment (i.e. increased stress, hypoxia) upon MI in vivo. Therefore, the cell survival is studied within the hybrid hydrogels using starred Live/Dead Assay including calcein AM (green) and ethidium homodimer (red) respectively. Assessment of cell survival not only provides the percentage of the live cells within various IPN hydrogels, but also allows identification of the location of the dead cells to study the formation of necrotic cores within the micro-tissues due to the diffusion limitations. Whether the cardiac cells are necrotic or apoptotic at the bottom of the microwells prior to encapsulation within the hybrid hydrogels is also investigated. Alexa 488 Annexin V conjugated apoptosis kit (Invitrogen, CA) are used to perform this assessment. The phenotype of cardiomyocytes within various the hybrid hydrogels is also studied. After 3, 7, 14 days culture of micro-tissues alone and with ECs (conditions b), IHC is performed (n=3 samples per condition) to stain for CMs specific markers including cardiac troponin complex (Tnl), myosin heavy chain (MHC), sarcomeric α-actinin and connexin-43 (Cx43). In all the conditions, the cells nuclei are stained with DAPI. Secondary antibodies are used as negative control. Another set of samples are used for protein analysis using western blotting technique to determine the level of sarcomeric α-actin, troponin-I and Cx43 expressions. Similar to step (a), the degree of capillary formation is assessed through IHC staining of HUVECs with CD31 and VE-cadherin protein markers.

In order to assess the electrophysiological characteristics of the injectable micro-tissues system, real time video microscopy is used 1) mono-culture of micro-tissues and 2) co-culture of micro-tissues with ECs within the hybrid hydrogels. The beating frequency (beats per min, BPM) of the cells is acquired from day 2 until day 7 of culture. The beating signal patterns are obtained using a custom written MATLAB program. To obtain statistically significant results, videos are taken from at least three replicates for each sample across all the experimental conditions. Furthermore, the samples are exposed to 2.3 mM fluo-4 AM and 0.1% Pluronic F-127 for 15 min at 37° C. After 15 min, the samples are washed 3 times in modified Tyrodes solution. Calcium transients are then imaged using a laser scanning confocal microscope. Furthermore, electrical stimulation is used to assess in vitro tissue functionality and maturity. To apply electrical stimulations, a custom-made setup is used based on established protocols (Annabi, N., et al. Advanced Functional Materials. 2013; 23:4950-4959). The samples are placed in culture media between two-carbon electrode (2-3 cm apart) connected to an electrical stimulator and an oscilloscope to measure the output signals. Biphasic square waveforms with 50 ms pulses are applied at amplitude of 0-7 V/cm and frequency of 1-3 Hz (Annabi, N., et al. Advanced Functional Materials. 2013; 23:4950-4959). Contractile ability of the constructs in response to electrical field is assessed using video-microscopy in a real time mode and excitation threshold is determined according to the minimum voltage for synchronous beating of CMs. All the recorded data is analyzed using MATLAB software. Next, endothelin-1, which is a well-known signaling pathway between ECs and CMs is blocked using bq-123 (Sigma) to study the effects of ECs:CMs paracrine signaling on the tissue contractility. Upon stimulation, IHC is performed to assess the expression of EC (CD31, VE-cadherin) and CM specific markers (sarcomeric α-actin, troponin-I and Cx43) as described previously.

Expected Results and Contingencies

The encapsulation of ECs within the hybrid hydrogels result in the formation of vascularized networks. Furthermore, co-culture of ECs along with micro-tissues lead to enhanced survival and functionalities (i.e. contractile behavior) of cardiac micro-tissues. In the event that problems such as lack of vascular formation occur, the concentration of vasculogenic peptide is increased, or the incorporation of pericyte cells is performed (1:3 ratio).

In case of weak cardiac cell contractility, the density of ECs is increased. In addition, in the case if the injection through the 30G needle results in clogging or damaging the micro-tissues, the size of the generated micro-tissues (20-40 µm in diameter) are decreased. The three top cell-embedded hydrogel that result in enhanced in vitro functionalities are used for in vivo studies. The specific criteria to select these candidates include: a) >90% cell survival, b) enhanced microvessel branching and density (4-6 branches per $mm^2$, 6-8 mm branch length), c) enhanced cardiac cells function in terms of spontaneous beating (60-80 beats per min), expression of cardiac Tn, sarcomeric α-actinin and Cx43 and excitation threshold (4 V for 1 Hz and 6 V for 1 Hz frequency).

The invention will now be illustrated by the following non-limiting Examples.

Examples

1. Polymer Synthesis

NIPAAm monomer was recrystallized from hexane, and AIBN initiator was recrystallized from methanol. Jeffamine® M-1000 acrylamide (JAAm) was synthesized in a reaction with Jeffamine® M-1000 and acryloyl chloride (Overstreet, D. J., et al. J Biomed Mater Res Part A. 2012; 101:1437-1446). Poly(NIPAAm-co-JAAm-co-HEMA), or PNJH was synthesized by free radical polymerization. Briefly, NIPAAm (7.5 g), JAAm (2 g), and HEMA (0.5 g) monomers were co-dissolved in THF, heated to 65° C., and the reaction was initiated with AIBN (83 mg). After 18 h, the PNJH product was redissolved in acetone, precipitated in cold ethyl ether, filtered, and vacuum dried. Poly(NIPAAm-co-JAAm-co-HEMA-acrylate), or PNJHAc, was synthesized by converting hydroxyl groups on the HEMA monomer to reactive acrylates, previously reported by Heffernan et al (Lee, B. H., et al. Biomacromolecules. 2006; 7:2059-2064; and Heffernan, J. M., et al. J. Biomed. Mater. Res. 2015; 104:17-25). Briefly, PNJH was dried overnight at 60° C. under vacuum and then dissolved at 10 wt % in THF with TEA (2.11 mL). The reaction was initiated by adding acryloyl chloride (1.21 mL) dropwise to the stirring solution while on ice. The product was precipitated in cold ether, filtered, and vacuum dried. PNJHAc was further purified by dialysis against diH2O (3500 MWCO) for 3 days. The lyophilized polymer was stored at −20° C. Dithiopropionic dihydrazide (DTPH) was prepared from DTPA using an established procedure (Vercruysse, K. P., et al, Bioconjugate Chem. 1997; 8:686-694). Thiolated gelatin (Gel-S) was synthesized from gelatin and DTPH using EDC chemistry based on previously reported studies (Heffernan, J. M., et al. Ann. Biomed. Eng. 2015; 43: 1965-1977; and Shu, X. Z., et al. Biomaterials 2003; 24: 3825-3834). To confirm the syntheses, proton nuclear magnetic resonance (1H NMR) spectra were recorded for PNJHAc and Gel-S with D20 as the solvent (400 MHz Varian liquid state NMR, Agilent Technologies, Santa Clara, Calif., USA), while Ellman's reagent test was used to measure the degree of thiolation (Ellman, G. L. Arch. Biochem. Biophys. 1959; 82: 70-77).

2. Preparation and Physical Characterization of the Hydrogel Matrix

To prepare the hydrogel samples for physical characterization, PNJHAc was dissolved (57.1 mg/mL) in Dulbecco's Phosphate Buffered Saline (DPBS). Subsequently, 40 mg/mL Gel-S in acidic DPBS (pH 3) was prepared at 37° C. for 5 min. The Gel-S solution was titrated with NaOH to increase the pH to 7, and then the two solutions were mixed to form the final product.

Scanning electron microscopy (SEM) (XL30 ESEM-FEG, USA) was utilized to evaluate the macroporous structure of the biohybrid hydrogels. Freshly made and hydrated (24 h at 37° C. in DPBS) samples were frozen in liquid nitrogen followed by lyophilization. Ten SEM images were acquired to analyze the porosity and pore size distribution of the hydrogel constructs using NIH ImageJ software. Briefly, the images were thresholded and the void area was calculated. In addition, pore size was quantified using the line tool. To evaluate swelling behavior of the PNJ-Gelatin biohybrid, hydrogel constructs were prepared and immediately soaked in vials of 5 mL DPBS and relocated at 37° C. for 48 h. The swollen hydrogels were removed at different time points and weighed. The swelling ratio defined as below (Eq. (1)):

$$\text{Swelling ratio} = \{(M_{wet} - M_{dry})/M_{dry}\} \qquad (1)$$

where, $M_{wet}$ is the mass of hydrated hydrogel and $M_{dry}$ is the mass of fresh hydrogel. Three identical samples were selected for each time point. Rheology was completed to quantify the viscoelastic characteristics of the temperature responsive polymer during both chemical (Michael-addition induced) and physical (temperature induced) crosslinking. Rheology solutions were prepared by separately dissolving PNJHAc (57.1 mg/mL) and Gel-S (40 mg/mL) in pH 3 DPBS. The solutions were then combined, titrated to ~pH 7 with 1 N NaOH, vortex mixed for 15 s, and positioned on a parallelplate rheometer (Anton Paar MCR-101). The storage and loss modulus in the solution and gel states were evaluated by a multistep temperature controlled procedure. In the first step, a time sweep was performed for 4 h at 25° C. to measure the gelation of PNJHAc and Gel-S. Next, the sample was subjected to controlled (0.5° C./min) and sustained heating (37° C. for 1 h) followed by quick cooling back to room temperature (25° C. for 1 h) to measure the reversible physical crosslinking of the PNJ-Gelatin hydrogel. To simulate the biophysical cues that cultured cardiac cells sense during the preparation and the first 12 h of culture, we performed a separate rheology measurement at 25° C. for 15 min (the sample preparation time) followed by immediate temperature increase to 37° C. for 12 h. In all experiments, an oscillatory 0.5% shear strain deformation was performed a frequency of 1 Hz, and normal force control was utilized to maintain constant contact between the gel and rotating head.

The LCST of PNJ-Gelatin following enzymatic digestion with collagenase was evaluated by cloud point measurement. PNJ-Gelatin was dissolved at 0.1 wt % in PBS at pH 7.4 in cuvettes and heated in a water bath from 25 to 37° C. in 1° C. increments and 40-75° C. in 5° C. increments. Samples were maintained at each temperature for at least 120 s before each measurement. Absorbance at 450 nm was recorded with a UV/Vis spectrometer (Pharmacia Biotech Ultrospec 3000). The LCST, which is defined as the temperature at 50% of the maximum absorbance, was then collected.

To assess hydrolytic degradation, hydrogel constructs were prepared and immediately placed in vials of 5 mL DPBS at 37° C. At different time points, constructs were immersed in liquid nitrogen, followed by lyophilization. Remaining mass percentage was defined as the lyophilized mass to the original one. Three identical samples were selected for each time point.

3. Cell Harvesting and Culture

Neonatal rat ventricular CMs were isolated from 2-day old pups according to the previously established protocol (Saini, H., et al. Adv. Healthc. Mater. 2015; 4: 1961-1971) accepted by the Institution of Animal Care at Arizona State University. The isolated cardiac cells were separated into CMs and CFs by pre-plating the cell suspension for 1 h and allowing CFs to attach to the tissue culture flask, due their higher adhesive nature compared to CMs (Saini, H., et al. Adv. Healthc. Mater. 2015; 4: 1961-1971; and Shin, S. R., et al. Acs Nano. 2013; 7:2369-2380). After 1 h, the harvested media, mainly containing CMs, was collected and used for further experimentation. We precisely isolated the ventricular tissue to minimize the presence of endothelial or smooth muscle cells, from the aorta region of the heart, within the isolated CMs population. However, the isolated CMs may still contain a few number of endothelial cells due to the presence of capillaries within the myocardial tissue. CMs and CFs were cultured in cardiac media containing Dulbecco's modified eagle medium (DMEM) (Gibco, USA), 10% fetal bovine serum (FBS) (Gibco, USA), L-Glutamine (1%) (Gibco, USA), and 100 units/mL of penicillin-streptomycin. Isolated cardiac cells were cultured under a static condition (no external electrical stimulation) and the cell culture media was changed every other day.

4. Preparation of the Biohybrid Cell-Laden Hydrogel

Figure 5:
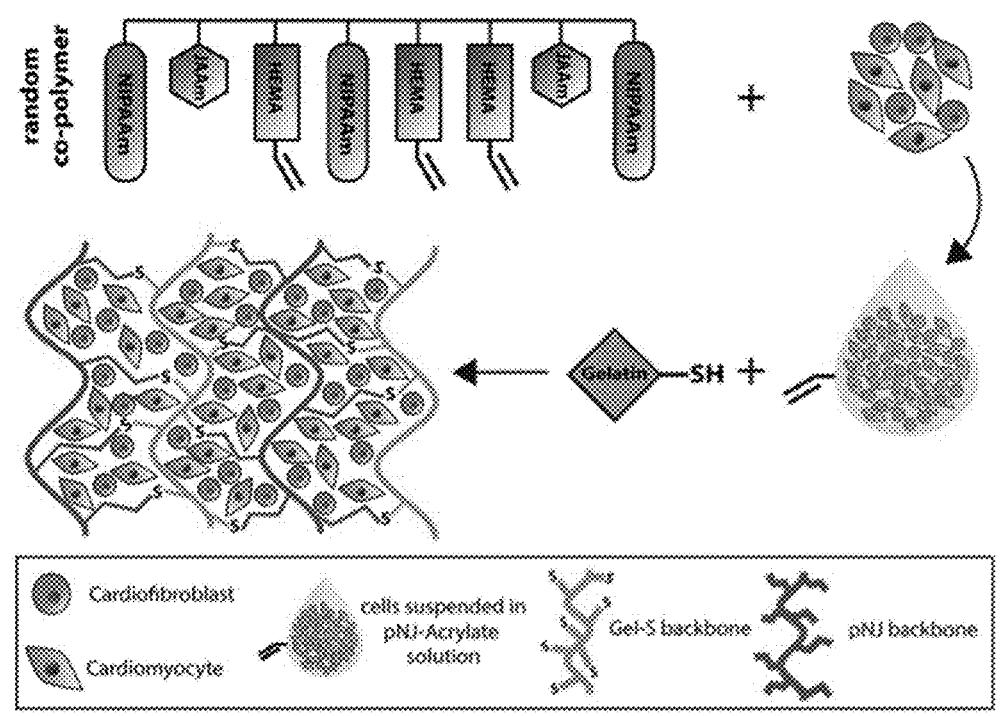
FIG. 5. The schematic displaying the fabrication procedure of the proposed injectable PNJ-Gelatin hydrogel with encapsulated CMs and CFs.

To prepare the cell-laden injectable PNJ-Gelatin biohybrid hydrogel, CMs (mono-culture condition) or a 2:1 ratio of CMs-CFs (co-culture condition) were dispersed ($35 \times 10^6$ cells/mL) in a solution of supplemented cardiac media containing 30% FBS and PNJHAc (57.1 mg/mL). Next, a 7.5 µL drop of cardiac cell suspension was placed on top of a sterile $18 \times 18$ mm$^2$ glass slide. Subsequently, a 7.5 µl Gel-S in cardiac media prepared at 40 mg/mL was mixed with the cell suspension with a final cell number of 525,000 CMs in mono-culture and 350,000 CMs and 175,000 CFs in co-culture conditions (FIG. 5). The prepared samples were chemically crosslinked in a 24-well plate at room temperature (25° C.) for 10 min followed by the addition of 0.5 mL of warmed cardiac media (37° C.) to initiate the physical crosslinking. The well plates were placed in humidified cell culture incubator (37° C. and 5% CO2) and subsequently cultured for a period of 9 days.

5. Cell Viability Assay

The survival of encapsulated cells within the PNJ-Gelatin hydrogel was evaluated on day 1 and 7 of culture, using a Live/Dead assay kit (Life technologies, USA) and following manufacturer protocol. Briefly, three individual samples of biohybrid hydrogels were selected for each type of culture (mono- and co-culture) and Zstack fluorescent images were acquired using an inverted microscope (Observer Z1, Zeiss, Germany) equipped with ApoTome.2 (Zeiss, Germany). The viability percentage was defined as number of viable cultured cardiac cells (green) divided by total number of cells.

6. F-Actin Staining and Fast Fourier Transform (FFT) Analysis

F-actin fibers were stained to visualize the cytoskeleton organization of cultured cells within the PNJ-Gelatin hydrogel in both mono- and co-culture groups on day 7 of culture. First, the cells were fixed in 4% paraformaldehyde (PF) for 30 min. Next, 1% (v/v) Triton x-100 was used to permeabilize the plasma membrane of the cells for 45 min at 25° C. Afterwards, the fixed cells were blocked in 1% (v/v) bovine serum albumin (BSA) (Sigma-Aldrich, USA) for 1 h at 4° C. Finally, the cells were stained with Alexa Fluor-488 phalloidin (1:40 dilution in 1% BSA, Life technologies, USA) for 1 h and counterstained with 40,6-diamidino-2-phenylindole dihydrochloride (DAPI, 1:10,000 dilution) for 30 min. A fluorescent microscope equipped with ApoTome.2 was utilized to take Z-stack fluorescent images through the samples. FFT images were further obtained and analyzed by means of ImageJ software (NIH) to assess the local organization of the F-actin fibers. To analyze the actin coverage area, the collected regions of interests, (ROIs) ($300 \times 300$ lm2), were quantified using NIH ImageJ software (n>10).

7. Immunostaining of Cardiac Specific-Markers

To investigate the phenotype of cultured cardiac cells (on day 7 of culture), immunostaining method was utilized according to previously developed protocols (Kharaziha, M., et al. Biomaterials. 2013; 34:6355-6366). Briefly, cells were fixed in 4% PF for 40 min followed by treatment with 0.1% Triton x-100 for 45 min at room temperature. Next, the cardiac cells were blocked in 10% goat serum for 2 h at 4° C. Afterwards, the fixed cells were stained with primary antibodies against sarcomeric a-actinin, connexin 43 (Abcam, USA) and troponin I (Developmental Studies Hybridoma Bank) (1:100 dilution in 10% goat serum) and placed in cold room (4° C.) for 24 h. After the primary staining, samples were washed five time with DPBS (5 min intervals) and stained overnight with secondary antibodies (Life Technologies, USA) comprised of Alexa Fluor-488 for sarcomeric α-actinin and troponin I, and Alexa Fluor-594 for connexin 43 (1:200 dilution in 10% goat serum). Next, cells were stained with DAPI (1:10,000 dilution in DPBS) for 30 min to label the nuclei. Finally, the stained samples were mounted and imaged (20× and 40×) using a ZEISS fluorescent microscope equipped with ApoTome.2. The average coverage area (n>12) for cardiac-specific proteins was assessed similar to Factin coverage analysis using NIH ImageJ software.

8. Quantitative Polymerase Chain Reaction (QPCR)

QPCR technique was used to evaluate the expression of certain cardiac specific genes (CTNT, CX43, ACTN1, and MLC2v) for both culture groups. Samples were selected at two considered time points (day 1 and 7 of culture encapsulated within the PNJGelatin hydrogel). For cell-laden matrices, the hydrogels were immersed in collagenase (Worthington Biochemical Corp., USA) solution (1 mg/mL) for 1 h at 37° C. to collect the encapsulated cardiac cells. After degradation of the hydrogel, the cell suspension was centrifuged at 1000 rpm for 5 min and the resulting supernatant was discarded. In the case of freshly isolated cells, the cell suspension was centrifuged at 1000 rpm for 5 min. RNA was isolated from cells using the NucleoSpin® RNA Kit (Clontech). Reverse transcription was performed with iScript Reverse Transcription Supermix for RT (Biorad). Quantitative PCR was carried out using TaqMan® Assays or SYBR® green dye on a BioRad CFX384 Touch™ Real-Time PCR Detection System. For the QPCR experiments run with TaqMan® Assays, a 10 min gradient to 95° C. followed by 40 cycles at 95° C. for 5 s and 60° C. for 30 s min was used. For QPCR experiments run with SYBR® green dye, a 2 min radient to 95° C. followed by 40 cycles at 95° C. for 15 s and 60° C. for 1 min was used. Gene expression was normalized to 18S rRNA levels. Delta $C_t$ values were measured as $C_t^{target} - C_t^{18s}$. All experiments were accomplished with two technical replicates and three biological replicates. Data were presented as the average of the biological replicates±standard error of the mean (SEM).

9. Evaluation of Spontaneous Tissue-Level Contraction

The spontaneous beating of CMs was monitored and measured every day during the culture period (9 days) using real-time optical microscopy. After detection of synchronous tissue-level (2.5×2.5 mm$^2$) beating, videos (n>12) were captured by using an inverted microscope equipped with an AxioCam MRm camera (Zeiss, Germany). Furthermore, representative beating signals were acquired using a custom written MATLAB code (Shin, S. R., et al. Acs Nano. 2013; 7:2369-2380). The amplitude and frequency variation indexes were calculated based on an original procedure developed by the authors. In detail, the collected beating signals of subsets (n=5, 0.5×0.5 mm$^2$) for each sample (n=4, 2.5×2.5 mm$^2$) were processed using MATLAB software to find the significant peaks. A significant peak was defined as below:

$$\text{Significant peaks} \geq (|\text{Amp}_{Median} - \text{Amp}_{Mean}| + \text{Amp}_{Mean}) \quad (2)$$

where $\text{Amp}_{Median}$ and $\text{Amp}_{Mean}$ were the median and mean amplitudes respectively. Next, the collected significant peaks (n>500) were normalized based on their average. The absolute difference between the normalized values and 1 was calculated to obtain the amplitude variation index. In the case of the frequency variation index, the related time for each significant peak was acquired and peak-to-peak time differences were calculated. Subsequently, the time differences were normalized to their average and the absolute difference between the normalized values and 1 was considered as the frequency variation index. Finally, the calculated indexes (n>20) were compared between mono- and co-culture groups.

10. External Electrical Stimulation

The response of the encapsulated cells (CMs and CFs), within the PNJ-Gelatin hydrogels, to external electrical stimulation was evaluated based on previously established protocol (Tandon, N., et al. Nat. Protoc. 2009; 4: 155-173). Briefly, a custom made chamber was assembled using two carbon electrodes (5 mm) with 1 cm spacing attached to a plastic petri dish (6 mm diameter) by silicon adhesive. Platinum wires were connected to the carbon electrodes (at the opposite ends of each electrode) and all connections were sealed using silicon adhesive. The entire chamber was washed with ethanol (70%) and put under UV light for 1 h for sterilization. To assess cardiac cells' response to the external electrical stimulation, pulsatile electrical signals (BK PRECISION 4052) with 3 ms duration at three different frequencies (1, 2, and 3 Hz) was applied in both mono- and co-culture conditions.

The minimum required voltage to obtain contraction of CMs was defined as the excitation threshold.

11. Statistical Analysis

The data was analyzed using t-test and ANOVA statistical methods. The results for viability, cytoskeleton, and cardiac specific markers coverage areas were reported as mean±standard deviation (SD). To determine a statistically significance difference between the groups, we used Tukey's multiple comparison test, with a p-value<0.05 considered to be significant. All the statistical analyses were performed by GraphPad Prism software (v.6, Graph-Pad San Diego).

Results

12. Preparation and Characterization of PNJ-Gelatin Hydrogel

Figure 6A:
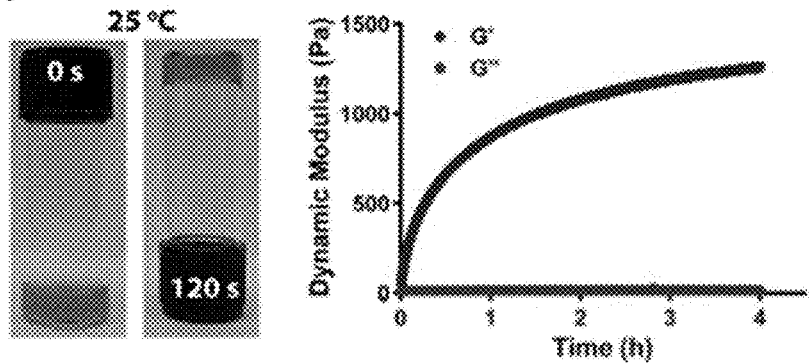
FIGS. 6A-6D. The viscoelastic behavior of PNJ-Gelatin hydrogel solutions at (FIG. 6A) room temperature (25° C. for 4 h), followed by measuring during controlled (0.5° C./min) and (FIG. 6B) sustained heating (37° C. for 1 h), and finally during (FIG. 6C) rapid cooling back to room temperature (25° C. for 1 h).
Figure 6B:
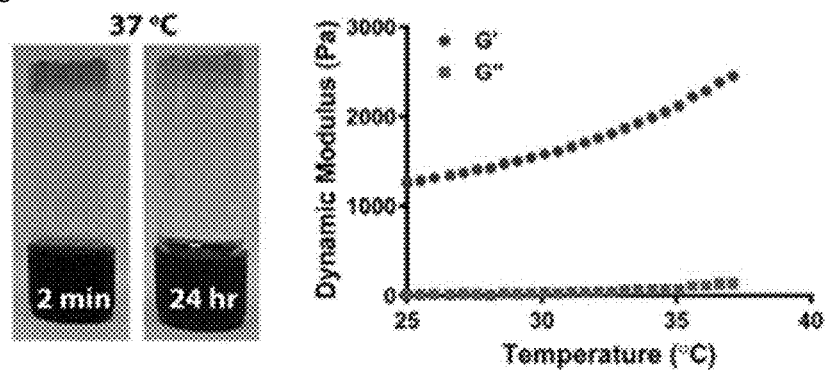
Figure 6C:
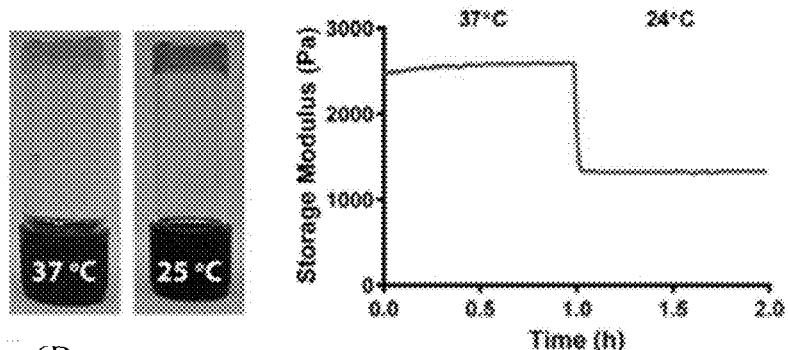
Figure 6D:
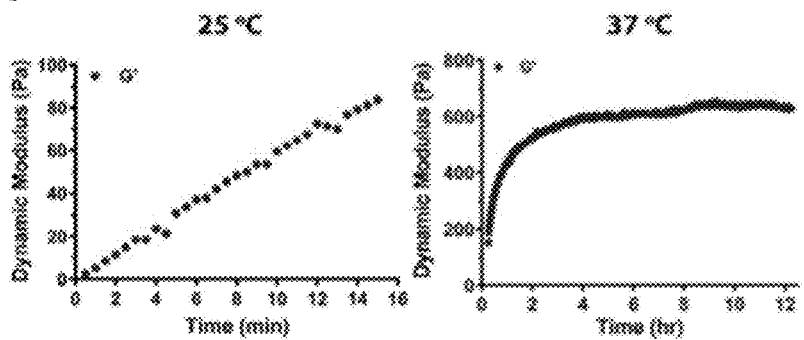

The PNJ-Gelatin hydrogel was obtained by mixing PNJHAc and Gel-S pre-polymer solutions at room temperature, which resulted in an orange solution followed by forming a soft gel after 120 s. FIG. 6A shows the viscoelastic characteristics of the hydrogel during the chemical crosslinking between PNJHAc and Gel-S. As can be seen in the graph, the storage modulus (G') increased over time and leveled out at approximately 4 h, indicating completion of chemical crosslinking. There was a sharp increase in G' (870 Pa) within the first hour of crosslinking, followed by a gradual increase to 1260 Pa up until 4 h. Furthermore, the hydrogel mainly exhibited elastic-behavior due to the negligible loss modulus (G", 19 Pa after 4 h). To further investigate the impact of the thermosensitivity of the NIPAAm component, the dynamic modulus was measured during a temperature ramp from 25° C. to 37° C. As shown in FIG. 6B, the rise in temperature induced an increase in the dynamic modulus of the PNJ-Gelatin hydrogel from 1260 to 2450 Pa, which indicated the occurrence of physical crosslinking. The dual-crosslinking (chemical and physical) nature of the biohybrid hydrogel was confirmed by dropping the temperature to 25° C. (FIG. 6C), which resulted in the same storage modulus (4 h) shown in FIG. 6A. Furthermore, the simulated rheology measurement (FIG. 6D) revealed that the cultured cells initially experienced a slight increase in the modulus up to 90 Pa within the first 15 min. Upon temperature increase occurring from the placement of the hydrogel samples in the incubator, the modulus increased as expected due to the crosslinking of PNIPAAm. To investigate the fate of the LCST after degradation of the gelatin, the PNJ-Gelatin hydrogel was degraded utilizing collagenase and cloud point measurements were taken of the degraded PNJ-Gelatin. The results indicated that LCST was 55° C. after enzymatic degradation, which is a temperature outside of physiological range. Therefore, it could be possible to utilize this degradation mechanism similar to previously developed degradable PNIPAM based hydrogels (Cui, Z., et al. Biomacromolecules. 2007; 8:1280-1286).

FIG. 7A illustrates the level of water content within the hydrogel constructs. Initially, the hydrogels swelled to 1.2 times their initial mass. After 48 h, hydration decreased to a stable level of 80%. Moreover, to investigate the macroporous architecture of the PNJ-Gelatin constructs, samples were characterized by SEM before and after hydration (24 h). FIG. 7B displays the hydrogel porosity percentage as an indicator of void spaces within the constructs. As can be seen, the porosity percentage slightly increased after hydration from 71.1%±1.5 to 75.6%±2.4. Furthermore, based on the SEM images (FIGS. 7C and 7D), the macroporous structures appeared to collapse and disorganize before hydration; however, once hydrated, morphology of the pores became more open, intact, and organized. These findings indicated that the absorbed water penetrated throughout the construct and inflated the pores. It was speculated that the average pore diameter would increase due to the higher hydration content, however no differences were observed (data not shown). Instead, the pore size distribution range expanded after hydration while maintaining the same average pore diameter (FIG. 7E).

13. Three-Dimensional (3D) Cell Culture and Survival

Figure 8A:
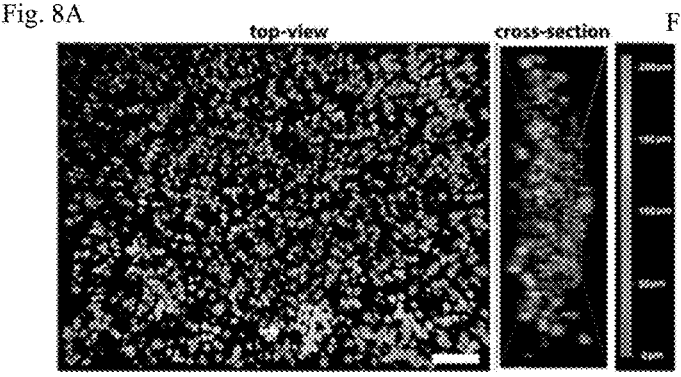
FIGS. 8A-8C. The 3D tissue construct and subsequent cytotoxicity assessment of the hydrogel.
Figure 8C:
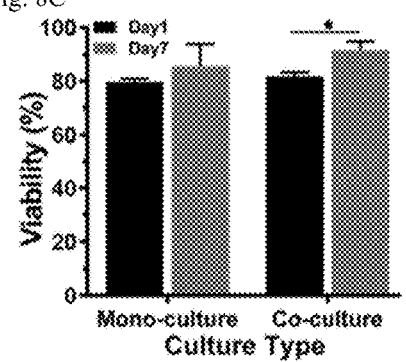
Figure 8B:
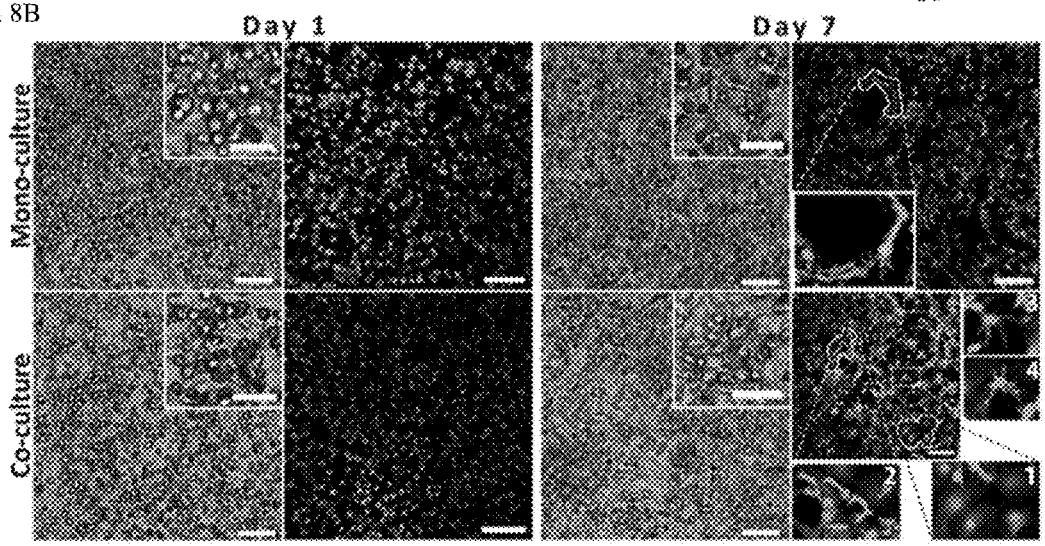

To demonstrate the capability of the PNJ-Gelatin hydrogel as a 3D microenvironment promoting cardiac cell adhesion, spreading, and survival, we encapsulated CMs (mono-culture) and a 2:1 ratio of CMs-CFs (co-culture) within the hydrogel matrix for a period of 9 days. We selected this ratio of CMs to CFs based on our recent study where we found the best viability, cell spreading and tissue-level functionalities (Saini, H., et al. Adv. Healthc. Mater. 2015; 4: 1961-1971). Z-stack images (FIG. 8A) confirmed successful fabrication of a homogenous 3D (150 lm thick) construct. FIG. 8B illustrates the changes in cell morphology as a function of time regardless of culture type. Phase contrast and fluorescent images were used to highlight the cell morphology (FIG. 8B) as well as cell viability (FIG. 8C). Both cell types encapsulated within the hydrogel matrix adopted a round morphology on day 1 of culture (FIG. 8B). The synthesized matrix supported the gradual spreading of both cells in the two culture conditions as a function of time. However, on day 4, the co-culture group demonstrated a higher number of elongated cardiac cells, whereas monoculture mostly exhibited cells with round morphology. In addition, round and elongated cardiac cells formed clusters in the co-culture group in comparison to separated arrangements of the cells in the mono-culture. By day 7, the CMs and CFs in the both culture groups exhibited higher numbers of elongated and spread cells in comparison to the first day (FIG. 8B). In particular, CFs demonstrated a larger cell area (FIG. 8B, co-culture inset #1) compared to CMs (FIG. 8B, mono-culture inset & co-culture inset #2). Interestingly, CMs in the co-culture exhibited small protrusions, which were rarely seen in mono-culture (FIG. 8B, co-culture inset #3 & 4). Overall, the cells exhibited well-connected structures in co-culture condition as compared to the mono-culture. FIG. 8C represents the quantitative results of the cell viability where both culture groups exhibited high levels of cell survival. Particularly, mono- and co-culture groups resulted in approximately 80% overall cell viability on day 1, while the average overall cell viability increased to 85% for mono-culture and 90% for co-culture by day 7. There were no statistically significant differences among the culture days for mono-culture. In contrast, due to the proliferative nature of CFs (Saini, H., et al. Adv. Healthc. Mater. 2015; 4: 1961-1971; and Sigel, A. V., et al. J. Mol. Cell. Cardiol. 1996; 28: 1921-1929), co-culture group exhibited an increase in overall cell viability (t-test (two tailed); $p<0.05$).

14. Assessment of Cytoskeleton Organization

Figure 9A:
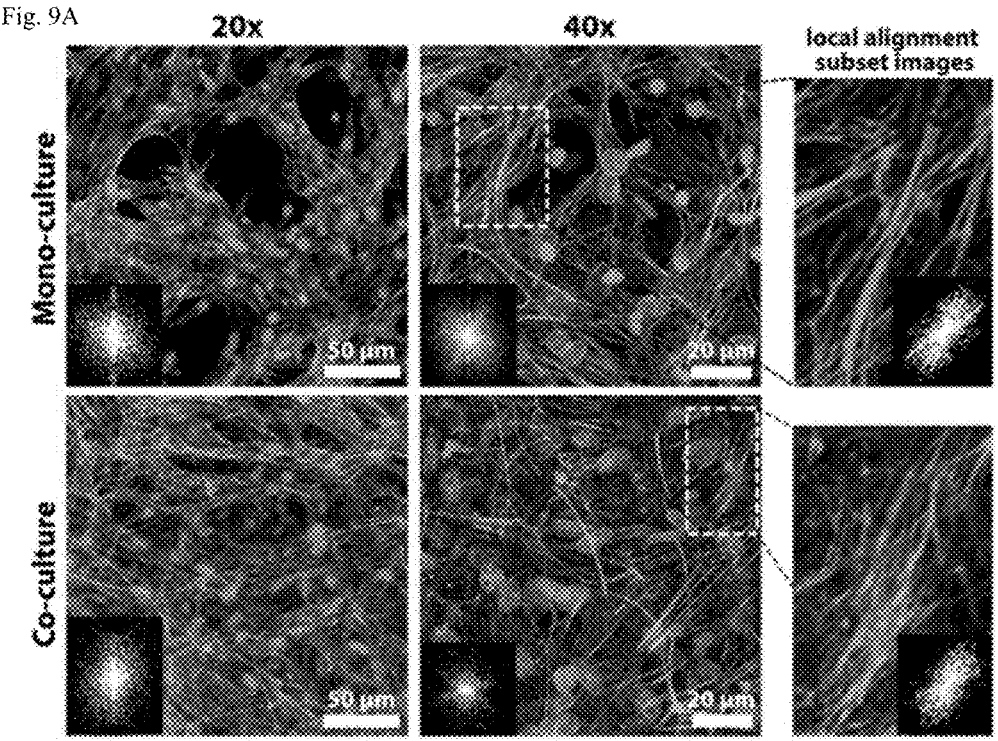
FIGS. 9A-9B. The cytoskeleton organization and analysis of F-actin fiber alignment within PNJ-Gelatin hydrogel.
Figure 9B:
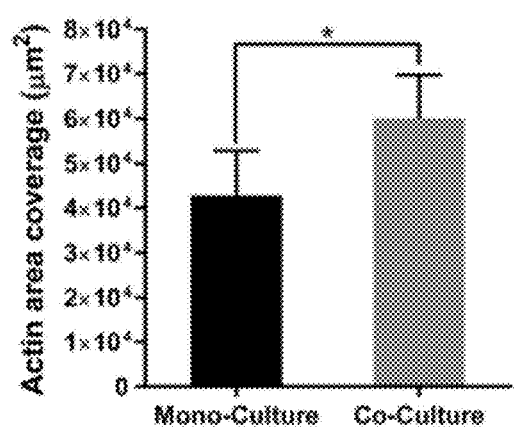

F-actin fibers were stained on day 7 of culture to determine the cytoskeleton organization and morphology of the cells in mono- and co-culture groups. Co-culture of the cells produced an intact and dense organization of cytoskeleton (F-actin) compared to mono-culture, which exhibited a discrete and loosely packed arrangement of F-actin fibers (FIG. 9A). These observations were consistent with phase contrast images demonstrating pronounced network of connected cells in the co-culture condition. Furthermore, FFT analysis was performed on 20× and 40× images to assess alignment of F-actin fibers (FIG. 9A, FFT insets). There were no overall tissue-level alignment, however, numerous local alignment were detected across both culture conditions. FFT images (dashed rectangles, subsets of 40× images in FIG. 9A) of small cell clusters illustrated the local cellular alignment. Additionally, the actin area coverage was analyzed within both culture conditions. As can be seen in FIG. 9B, a significant difference ($p<0.05$) in terms of actin coverage was observed between the culture groups pointing to the contributions of CFs in assembling a dense cell organization in co-culture condition (Saini, H., et al. Adv. Healthc. Mater. 2015; 4: 1961-1971).

15. Analyses of Cardiac-Specific Markers

Figure 10:
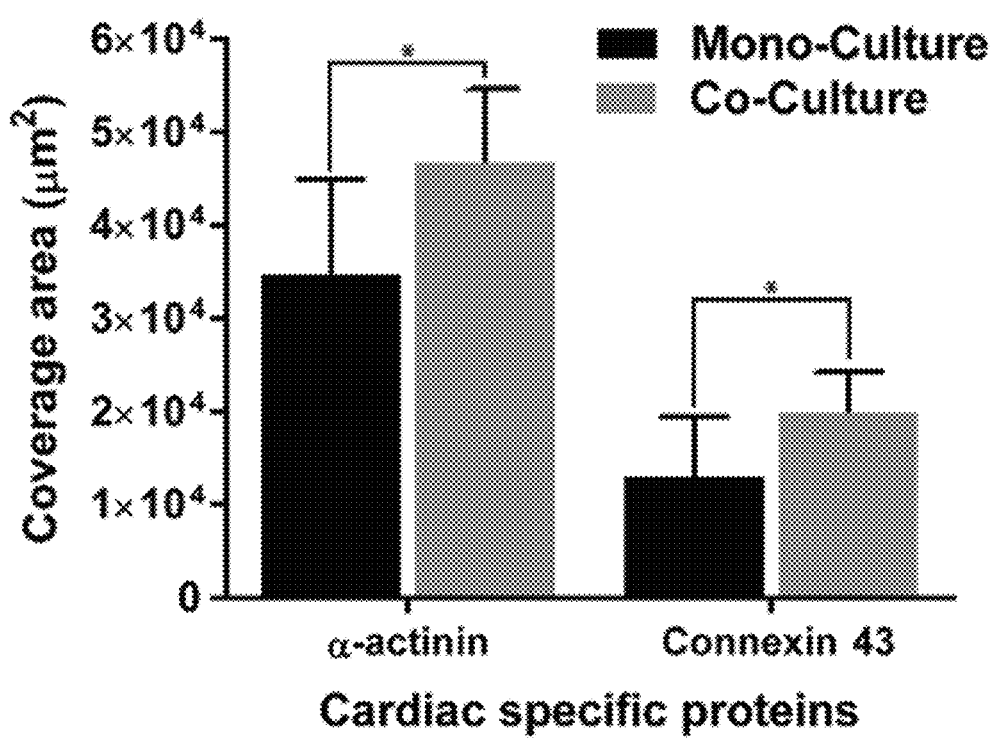
FIG. 10. The average coverage area ($\mu m^2$) of sarcomeric α-actinin and connexin 43 proteins at day 7 (n>12; *p<0.05).

Sarcomeric α-actinin, troponin I, and connexin 43 (cardiac-specific markers) were stained to assess cardiac cells phenotype within the PNJ-Gelatin biohybrid hydrogel. The fluorescence coverage area (FIG. 10), correlating to the architecture and distribution of expressed cardiac proteins, was quantified based on 20× immunostained images. Sarcomeric α-actinin and connexin 43 displayed statistically (t-test (two tailed); $p<0.05$) higher coverage area in co-culture condition. The cells exhibited a well distribution of troponin I in both culture conditions. Overall, the presence of CFs assisted CMs to connect and form cell-cell junctions (as indicated by connexin 43), producing well-distributed and connected clusters of cells.

To demonstrate that encapsulation and subsequent culture of cardiac cells within the PNJ-Gelatin hydrogel did not alter their gene expression profile, we performed QPCR analysis on day 1 and 7. This analysis revealed that there were no statistically significant (t-test (two tailed); $p>0.05$) changes in expression of CMs specific genes including cTNT, MLC2v, ACTN1, and CX43 in both the mono- and co-culture condition over the course of 7 days of culture.

16. Beating Behavior of the Encapsulated Cardiac Cells

Figure 11A:
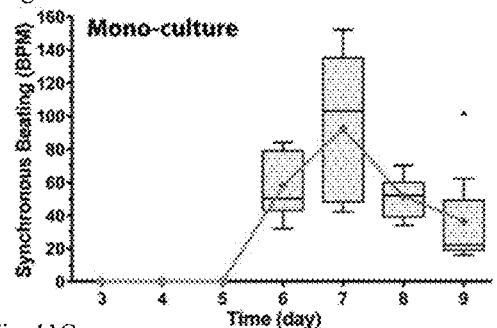
FIGS. 11A-11F. Tissue-level beating and synchrony assessment of cultured cardiac cells within the PNJ-Gelatin hydrogel. The average number of beats per minute (BPM) for (FIG. 11A) mono- and (FIG. 11B) co-culture groups from day 3 to 9 of culture.
Figure 11B:
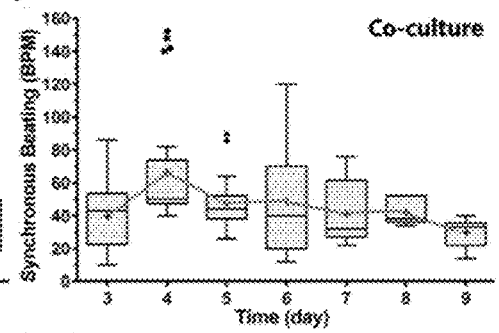

Beating behavior of cardiac cells was examined by analyzing the number of tissue-level (2.5×2.5 mm$^2$ field of view) synchronous contraction in a daily manner. The results in FIGS. 11A and 11B show the average number of beats per minute (BPM) within both mono- and co-culture groups. In mono-culture, the encapsulated cardiac cells started beating individually on day 3. As the cells came into contact with each other, they demonstrated a synchronized beating behavior starting at day 6 of culture (57±19 BPM) (FIG. 11A). These observations were consistent with network formation of the cells based on the phase contrast and fluorescence images (FIG. 8B). The BPM reached the highest value (92±42 BPM, $p<0.05$) on day 7 followed by a significant decline to 36±28 BPM by day 9. Additionally, the beating behavior was not maintained uniformly over the culture period (unstable trend represented by the blue line). On the other hand, the co-culture group (FIG. 11B) exhibited synchronous beating as early as day 3 of culture (39±20 BPM) and maintained a stable trend (represented by the blue line) in terms of BPM up to day 9 (30±8 BPM).

Figure 11C:
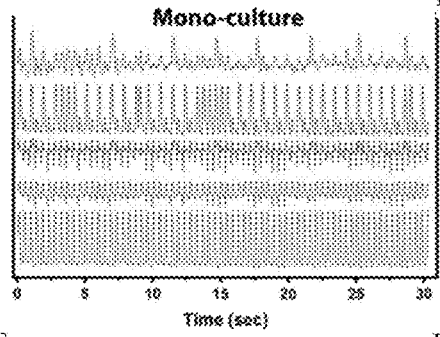
Figure 11D:
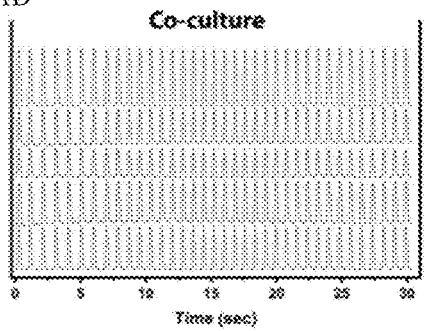
Figure 11E:
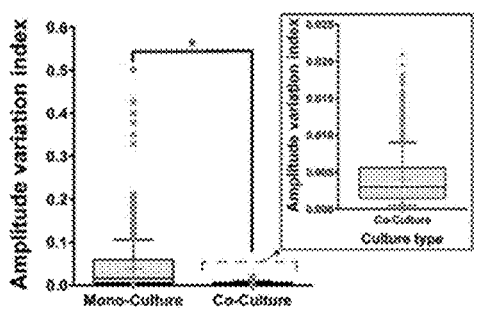
Figure 11F:
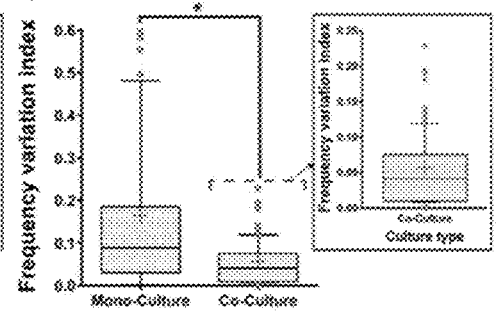
Figure 12:
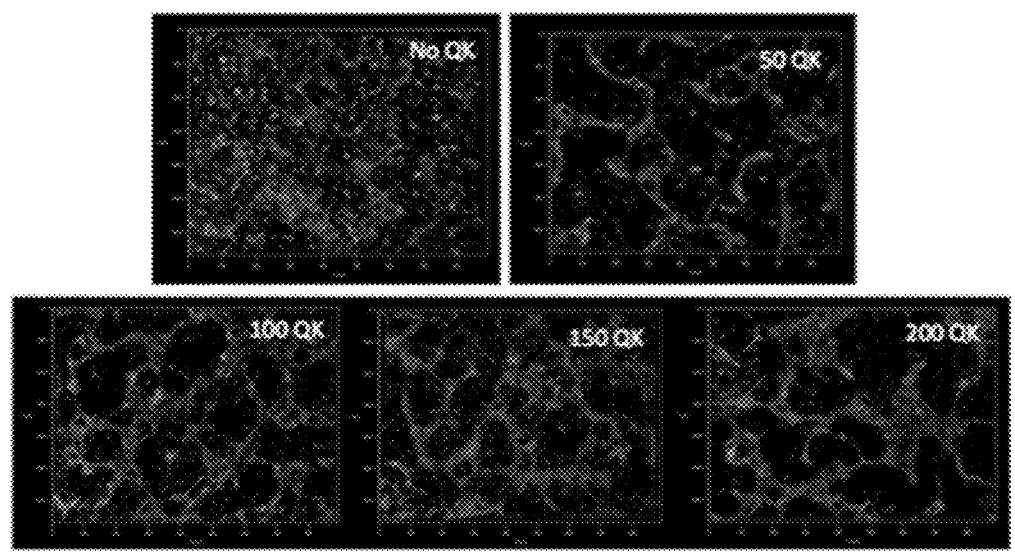
FIG. 12. Vascular formation within the proposed injectable hydrogels.

To further investigate contraction signal synchrony in terms of amplitude and frequency, the tissue-level field of view (2.5×2.5 mm$^2$) was subdivided in to 0.5×0.5 mm$^2$ subsets. FIGS. 11C and 11D show beating signals of subsets within a single representative field of view. As can be seen, the mono-culture signals displayed high fluctuations in peak to peak amplitude and period whereas co-culture condition exhibited uniform signals. Furthermore, similar frequencies between subset signals were observed for co-culture, whereas such behavior was not seen in monoculture of the CMs. These findings indicated that the different subset areas within one field of view for the co-culture group were in synchrony compared to the mono-culture condition. Moreover, amplitude and frequency variation indexes were developed to further quantitatively analyze the tissue-level synchrony. Amplitude and frequency variations were found to be significantly lower in co-culture compared to mono-culture, indicating higher tissue-level synchrony in the co-culture condition (FIGS. 11E and 11F).

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A temperature-responsive dual-gelling hydrogel comprising hydrogel polymers and a polymer cross-linking moiety, wherein the lower critical solution temperature (LCST) of the hydrogel polymers is less than 37° C. and the polymer cross-linking moiety is capable of chemically cross linking to the hydrogel polymers to form a polymer matrix, wherein the hydrogel polymer comprises monomers of N-isopropylacrylamide (NIPAAm), Jeffamine M-1000 acrylamide (JAAm) and hydroxylethyl methacrylate (HEMA), and wherein the hydrogel polymer is poly(NIPAAm-co-JAAm-co-HEMA).

2. The temperature-responsive dual-gelling hydrogel according to claim 1, wherein the hydrogel polymer comprises monomers of N-isopropylacrylamide (NIPAAm), R-α-Acryloyloxy-β, β-dimethyl-γ-butyrolactone (DBLA), Jeffamine M-1000 acrylamide (JAAm) and N-acryloylacrylamide (NAA).

3. The temperature-responsive dual-gelling hydrogel of claim 2, wherein the hydrogel polymer is poly(NIPAAm-co-DBLA-co-JAAm-co-NAA).

4. The temperature-responsive dual-gelling hydrogel according to claim 1, wherein the HEMA monomers comprise hydroxyl groups and at least one of the hydroxyl groups on the HEMA monomers is converted to an acrylate group.

5. The temperature-responsive dual-gelling hydrogel of claim 4, wherein the hydrogel polymer is poly(NIPAAm-co-JAAm-co-HEMA-acrylate).

6. A temperature-responsive dual-gelling hydrogel comprising a plurality of hydrogel polymers and a polymer cross-linking moiety, wherein the lower critical solution temperature (LCST) of the hydrogel polymers is less than 37° C. and the polymer cross-linking moiety is capable of chemically cross linking to the hydrogel polymers to form a polymer matrix, wherein the hydrogel polymer is poly (NIPAAm-co-JAAm-co-HEMA) and the polymer cross-linking moiety is thiolated gelatin, and wherein the HEMA monomers comprise hydroxyl groups and at least one of the hydroxyl groups on the HEMA monomers is converted to an acrylate group.

7. A method for manufacturing a harvestable micro-tissue embedded hydrogel comprising culturing the harvestable micro-tissue within the hydrogel of claim 1.

8. The method of claim 7 further comprising seeding one or more microwells with a cell culture solution and incubating the microwells under conditions suitable for the formation of micro-tissues.

9. The method of claim 7, wherein the cells are cardiac cells.

10. A hydrogel according to claim 1 for use in therapy.

11. A hydrogel according to claim 1 for use in the treatment of a myocardial infarction.

12. A method for delivering cells to an infarct region in a mammal in need of such treatment comprising administering a temperature-responsive dual-gelling hydrogel as described in claim 1 to the mammal thereof.

13. The temperature-responsive dual-gelling hydrogel of claim 1, further comprising cardiac cells.

14. The temperature-responsive dual-gelling hydrogel of claim 13, wherein the cardiac cells are cardiomyocytes (CMs).

15. The temperature-responsive dual-gelling hydrogel of claim 13, wherein the cardiac cells are cardiomyocytes (CMs) and cardiac fibroblasts (FMs).

16. The temperature-responsive dual-gelling hydrogel of claim 15, wherein the ratio of CMs to FMs is about 2:1.

17. A method for manufacturing a harvestable micro-tissue embedded hydrogel comprising culturing the harvestable micro-tissue within the hydrogel of claim 4.

18. A method for manufacturing a harvestable micro-tissue embedded hydrogel comprising culturing the harvestable micro-tissue within the hydrogel of claim 6.

19. A hydrogel according to claim 4 for use in therapy.

20. A method for delivering cells to an infarct region in a mammal in need of such treatment comprising administering a temperature-responsive dual-gelling hydrogel as described in claim 4 to the mammal thereof.

* * * * *